US006764661B1

(12) United States Patent
Girard

(10) Patent No.: US 6,764,661 B1
(45) Date of Patent: Jul. 20, 2004

(54) DEVICE FOR PRODUCING AN AQUEOUS CHLORINE DIOXIDE SOLUTION

(75) Inventor: J. Blair Girard, Newcastle, OK (US)

(73) Assignee: Avantec Technologies, Inc., Columbus, OH (US)

( * ) Notice: Subject to any disclaimer, the term of this patent is extended or adjusted under 35 U.S.C. 154(b) by 693 days.

(21) Appl. No.: 09/605,689

(22) Filed: Jun. 27, 2000

(51) Int. Cl.[7] .......................... A61L 9/015; C01B 11/24
(52) U.S. Cl. .......................... 422/305; 422/120; 222/3; 252/187.21; 423/477
(58) Field of Search ................................. 422/120, 122, 422/305; 222/3; 426/408, 561; 99/467, 474, 485; 423/477; 252/187.21

(56) References Cited

U.S. PATENT DOCUMENTS

| | | | |
|---|---|---|---|
| 2,022,262 A | 11/1935 | White ........................ 87/5 |
| 2,071,091 A | 2/1937 | Taylor ...................... 167/17 |
| 2,071,094 A | 2/1937 | Vincent ..................... 167/17 |
| 2,482,891 A | 9/1949 | Aston ....................... 252/187 |
| 3,591,515 A | 7/1971 | Lovely ...................... 252/187 |
| 4,104,190 A | 8/1978 | Hartshorn .................. 252/187 |
| 4,200,610 A | 4/1980 | Swaine et al. | |
| 4,547,381 A | 10/1985 | Mason et al. ............... 426/316 |
| 4,585,482 A | 4/1986 | Tice et al. ................ 106/15.05 |
| 4,593,040 A | 6/1986 | Adam et al. ................ 514/395 |
| 4,689,169 A | 8/1987 | Mason et al. .......... 252/186.24 |
| 4,731,193 A | 3/1988 | Mason et al. ............... 252/95 |
| 4,975,277 A | 12/1990 | Janisiewicz et al. ........ 424/93 |
| 5,008,096 A | 4/1991 | Ringo ....................... 423/477 |
| 5,091,107 A | 2/1992 | Hutchings | |
| 5,215,747 A | 6/1993 | Hairston et al. ............. 424/93 |
| 5,278,112 A | 1/1994 | Klatte ...................... 502/62 |
| 5,314,852 A | 5/1994 | Klatte ...................... 502/60 |
| 5,334,619 A | 8/1994 | Vaughn et al. ............. 514/675 |
| 5,387,207 A | 2/1995 | Dyer et al. ................ 604/369 |
| 5,567,405 A | 10/1996 | Klatte et al. ............... 423/477 |
| 5,703,948 A | 12/1997 | Yanovsky ................... 380/21 |
| 5,705,092 A | 1/1998 | Wellinghoff et al. ... 252/187.21 |
| 5,707,546 A | 1/1998 | Pitochelli ............... 252/187.21 |
| 5,707,739 A | 1/1998 | Wellinghoff et al. ........ 428/403 |
| 5,777,850 A | 7/1998 | Jakob et al. ................ 361/736 |
| 5,851,374 A | 12/1998 | Cowley et al. ............. 205/471 |
| 5,853,689 A | 12/1998 | Klatte ...................... 423/478 |
| 5,885,543 A | 3/1999 | Klatte ...................... 423/477 |
| 5,895,638 A | 4/1999 | Tenney ..................... 423/478 |
| 6,015,935 A | 1/2000 | LaVon et al. ............... 604/378 |
| 6,238,643 B1 | 5/2001 | Thangaraj et al. | |

FOREIGN PATENT DOCUMENTS

| | | |
|---|---|---|
| CA | 959238 | 12/1974 |
| EP | 0 360 794 B1 | 8/1994 |
| WO | WO 99/24356 | 5/1999 |

Primary Examiner—Robert J. Warden, Sr.
Assistant Examiner—Sean E. Conley
(74) Attorney, Agent, or Firm—Speckman Law Group

(57) ABSTRACT

A device for producing an aqueous chlorine dioxide solution when placed in water. The device includes a membrane shell that defines a compartment which includes one or more dry chemicals (e.g., a metal chlorite and an acid) capable of producing chlorine dioxide gas when exposed to water. Wick means extend into the compartment for absorbing water and transporting water into the compartment such that the chemical(s) in the compartment dissolve in the water and produce chlorine dioxide. In one embodiment, the membrane is formed of a material that allows the passage of gas (e.g., chlorine dioxide) but is impervious to liquid (e.g., water). In another embodiment, the wick means is a wick member which divides the compartment into first and second compartment sections. One chemical (metal chlorite, for example) is contained within the first compartment section and another chemical (acid, for example) is contained within or can easily be placed in the second compartment section. When the device is placed in water, water enters the device by way of the wick means and possibly the membrane shell. The chemicals dissolve in the water and react to produce chlorine dioxide gas. The chlorine dioxide gas then passes through the membrane shell and possibly the wick member into the surrounding water transforming the water into an aqueous chlorine dioxide solution. The solution can then be used, for example, as a disinfectant solution.

57 Claims, 12 Drawing Sheets

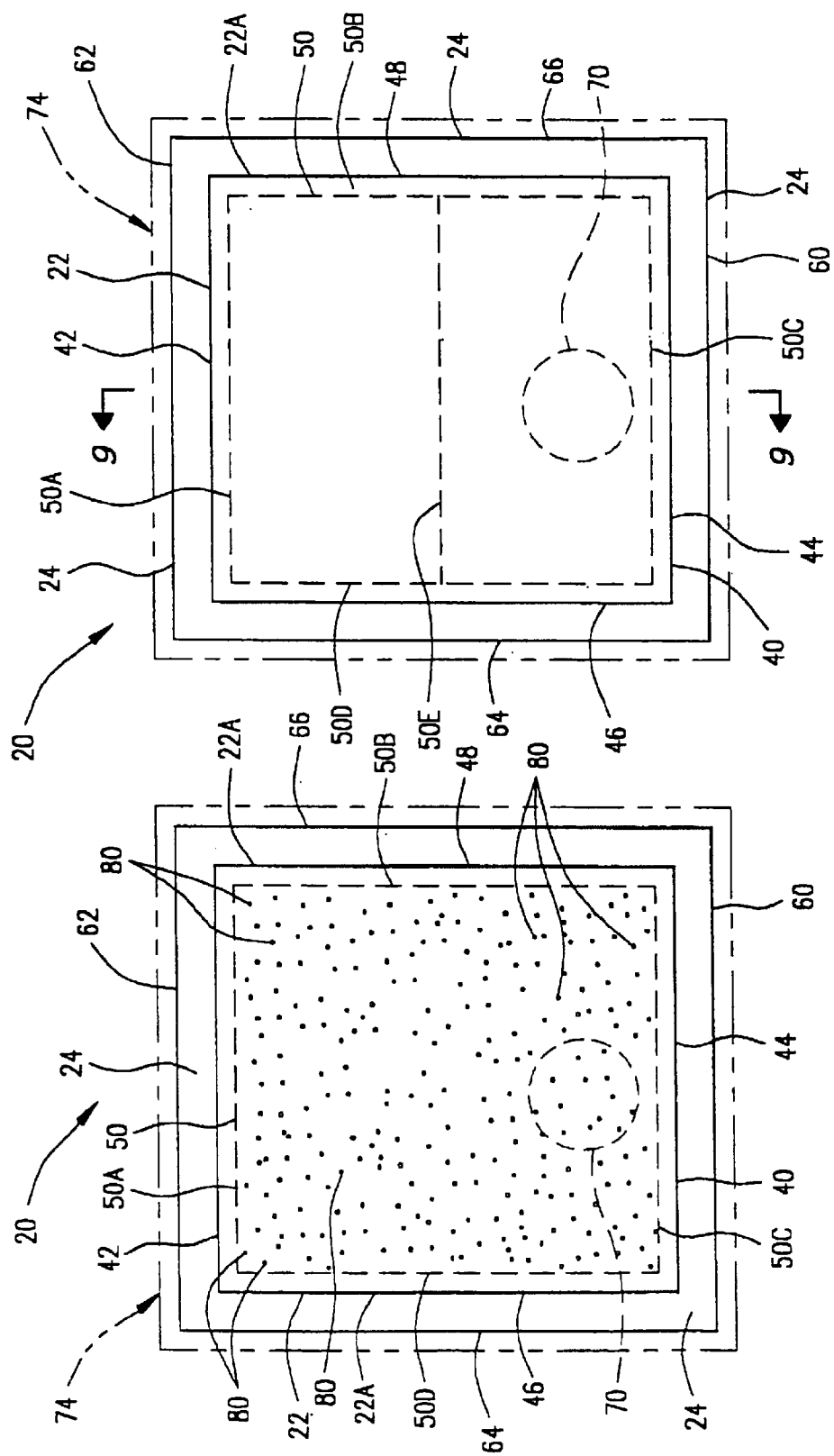

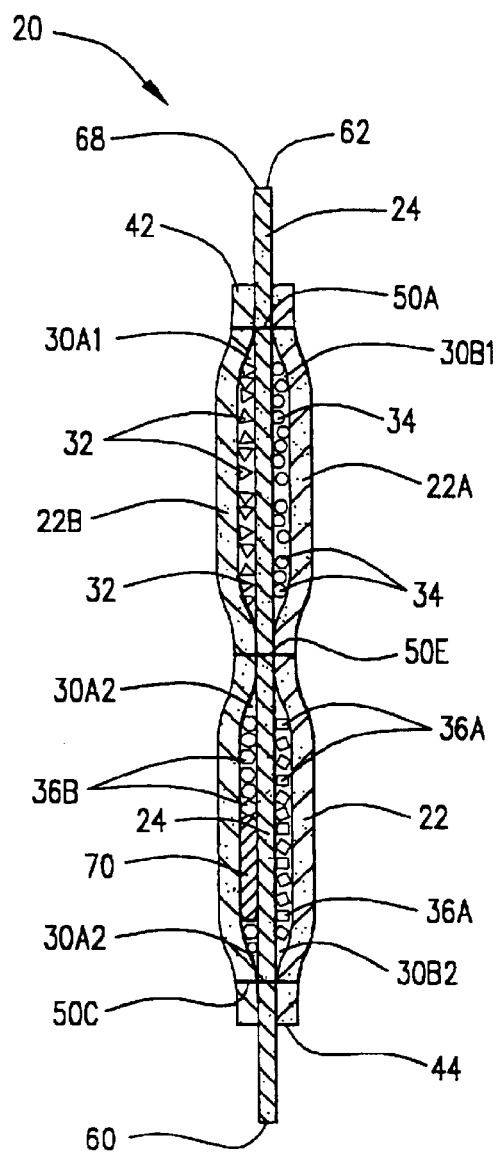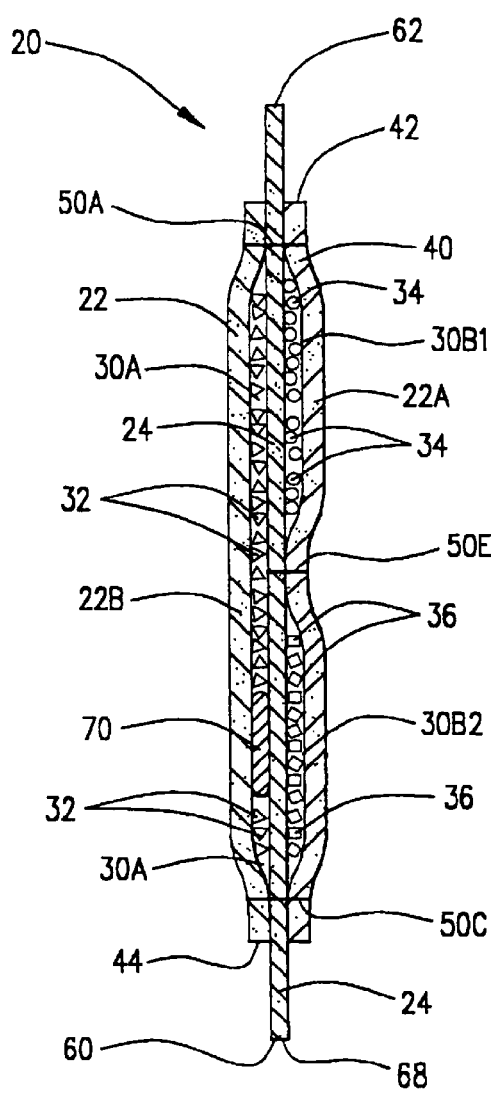
FIGURE 9
FIGURE 10

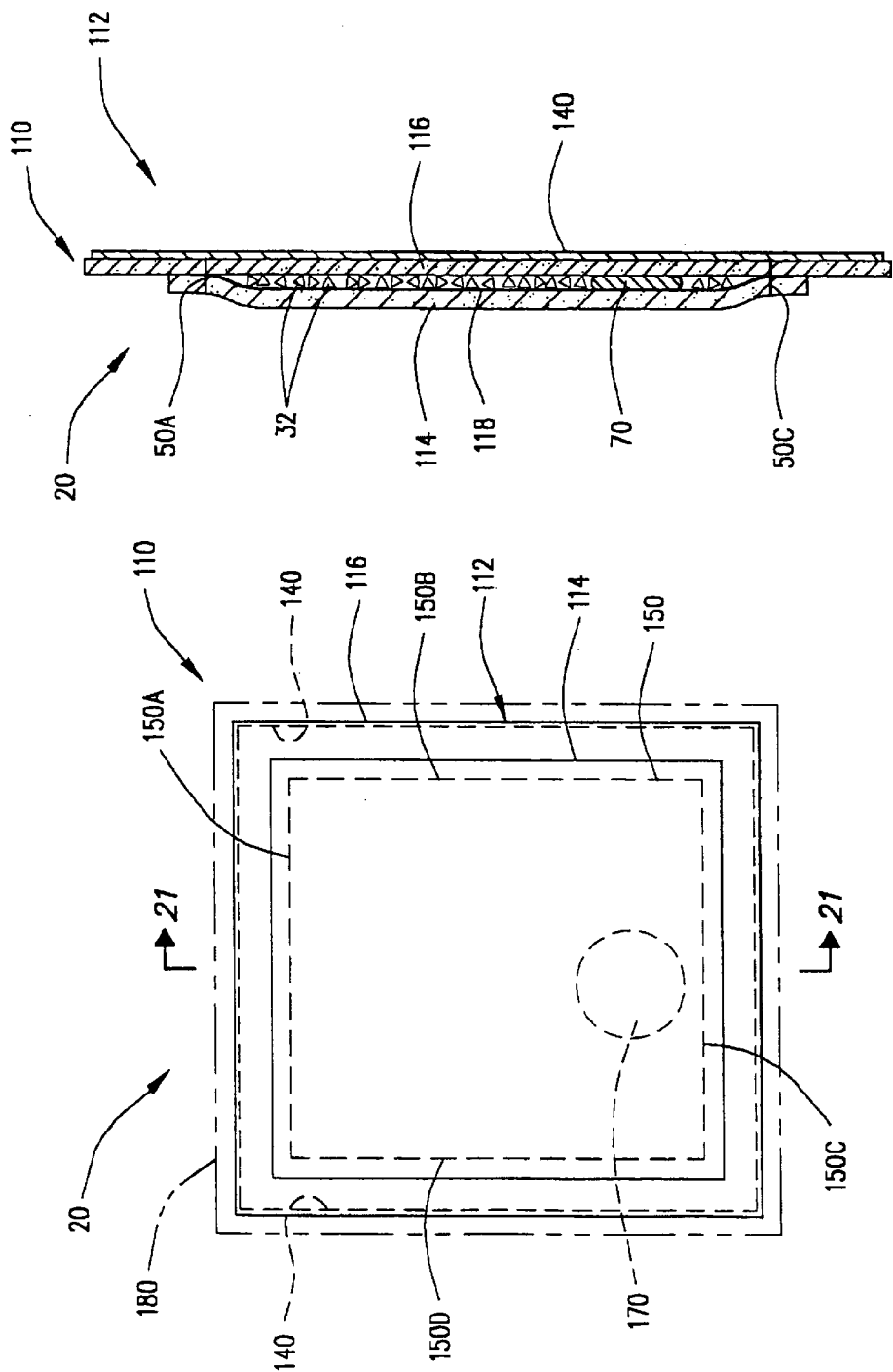

DEVICE FOR PRODUCING AN AQUEOUS CHLORINE DIOXIDE SOLUTION

BACKGROUND OF THE INVENTION

This invention relates generally to apparatus and methods for producing aqueous chlorine dioxide solutions, and particularly to such apparatus and methods that utilize dry chemicals that react to form chlorine dioxide when exposed to water.

Chlorine dioxide is an excellent disinfectant and oxidizer with bleaching, deodorizing, bactericidal, viricidal, algicidal and fungicidal properties. It is frequently used to control microorganisms on or around foods because it destroys the microorganisms without forming byproducts that pose a significant adverse risk to human health, e.g., chloramines and chlorinated organic compounds. Chlorine dioxide is an effective antimicrobial agent at a concentration as low as 0.1 ppm and over a wide pH range. It is thought to penetrate cell walls and cell membranes and react with vital amino acids in the cytoplasm of the cell to kill the organism.

Unfortunately, chlorine dioxide is not stable during storage and can be explosive at high concentrations. As a result, chlorine dioxide gas is not produced and shipped under pressure. It must generally be generated on site using conventional chlorine dioxide generators or other means of generation. Conventional chlorine dioxide generation can be carried out in an efficient manner in connection with large-scale operations such as those in pulp and paper or water treatment facilities. In other applications, however, generating chlorine dioxide on site is not a good option. Conventional on-site chlorine dioxide generation can be costly, cumbersome and difficult because of the need for a generator and the need to handle the generator and the chemicals associated with the generation process.

Chlorine dioxide can also be generated by combining chlorite anions and acid in an aqueous solution. Typically, an acid is added to a solution containing in the range of from about 0.01 to about 32 percent by weight sodium chlorite and having a pH in the range of from about 8 to about 13. The acid can be any acid capable of lowering the pH of the solution to a level below about 7. For example, when approximately 10 grams of citric acid powder are added to an aqueous solution containing approximately 3.35% by weight sodium chlorite, the pH of the solution is lowered to about 2.9 and a solution containing approximately 7% by weight chlorine dioxide is formed.

A solution of a metal chlorite and water wherein the pH of the solution is maintained at 8 or above is sometimes referred to as a stabilized chlorine dioxide solution. Unfortunately, stabilize chlorine dioxide solutions are of limited use if they are needed at remote locations because of the difficulty and expense associated with handling and shipping the solutions. Also, in order to activate a "stabilized" chlorine dioxide solution, the pH of the solution must be lowered to below 5, typically to a range of from about 2 to about 3. Although lowering the pH of the solution to such a level can be done on site, it is not typically a good alternative because of the danger associated with handling acids manually (e.g., the danger associated with inadvertent skin contact and inhalation of acid vapors).

In order to avoid the difficulty of using conventional chlorine dioxide generators, the expense associated with handling and shipping stabilized chlorine dioxide solutions and related precursor solutions and the dangers associated with activating chlorine dioxide solutions, dry compositions containing chemicals (e.g., sodium chlorite and acid) that react to form chlorine dioxide when placed in water have been developed. The compositions can be easily shipped to remote locations in dry form. The necessary water can be merely added on site. For example, in an application wherein a disinfectant solution is needed to clean surfaces, a dry composition containing a metal chlorite and an acid can be mixed with water on site which causes the components to react and produce an aqueous chlorine dioxide solution. The solution is then used to disinfect the surfaces. The aqueous chlorine dioxide solution is produced (chlorite anion is converted to chlorine dioxide) according to the following equation:

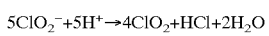

$$5ClO_2^- + 5H^+ \rightarrow 4ClO_2 + HCl + 2H_2O$$

Dry compositions for generating chlorine dioxide solutions are known in the art. For example, U.S. Pat. No. 2,022,262, issued to White on Nov. 26, 1935, discloses stable stain-removing compositions made from a dry mixture of water-soluble alkaline chlorite salt, an oxalate and an acid. U.S. Pat. No. 2,071,091, issued to Taylor on Feb. 16, 1937, discloses the use of chlorous acid and chlorites to kill fungi and bacterial organisms by exposing the organisms to the compounds at a pH of less than about 7. The patent also discloses using dry mixtures of chlorites and acids to produce stable aqueous solutions useful as bleaching agents. U.S. Pat. No. 2,482,891, issued to Aston on Sep. 27, 1949, discloses stable, solid, substantially anhydrous compositions comprising alkaline chlorite salts and organic acid anhydrides which release chlorine dioxide when contacted with water.

Canadian Patent No. 959,238, issued to Callerame on Dec. 17, 1974, discloses using two water-soluble envelopes, one containing sodium chlorite and one containing an acid, to generate chlorine dioxide. The envelopes are placed in water and the sodium chlorite and acid dissolve in the water and react to produce a chlorine dioxide solution. U.S. Pat. No. 2,071,094, issued to Vincent on Feb. 16, 1937, discloses deodorizing compositions in the form of dry briquettes formed of a mixture of soluble chlorite, an acidifying agent, and a filler of relatively low solubility. Chlorine dioxide is generated when the briquettes contact water.

U.S. Pat. No. 4,585,482, issued to Tice et al. on Apr. 29, 1986, discloses a long-acting biocidal composition comprising a microencapsulated mixture of chlorite and acid that when added to water releases chlorine dioxide. The primary purpose of the microencapsulation is to provide for hard particles that will be free flowing when handled. The microencapsulated composition also protects against water loss from the interior of the microcapsule. The microcapsules produce chlorine dioxide when immersed in water. Unfortunately, the microcapsules release chlorine dioxide relatively slowly and are therefore not suitable for applications that require the preparation of chlorine dioxide on a relatively fast basis.

PCT Application PCT/US98/22564 (WO 99/24356), published on May 20, 1999, discloses a method and device for producing chlorine dioxide solutions wherein sodium chlorite and an acid are mixed and enclosed in a semi-permeable membrane device. When the device is placed in water, water penetrates the membrane. The acid and sodium chlorite dissolve in the water and react to produce chlorine dioxide. The chlorine dioxide exits the device through the membrane into the water in which the device is immersed producing a chlorine dioxide solution that can be used as an antimicrobial solution or for other purposes. The primary disadvantage of the disclosed device and method is that ambient moisture can penetrate the semi-permeable membrane and initiate the reaction prematurely.

In general, the prior art devices and methods using membranes are susceptible to premature activation by water or water vapor and therefore have a reduced shelf life unless sufficient steps are taken to protect the devices from exposure to ambient moisture or water. Such devices and methods are typically slow to interact with water and produce the desired chlorine dioxide. Also, in order to comply with U.S. Department of Transportation and other regulations, many prior art devices require that special and sometimes burdensome handling and shipping procedures be utilized in connection with the devices. For example, if sodium chlorite and acid are packaged together, certain restrictions may apply.

As a result, there is a need for a device for producing an aqueous chlorine dioxide solution that has an extended shelf life compared to prior art devices, that is not susceptible to activation by ambient moisture, that forms a chlorine dioxide solution much more quickly than prior art devices and that can be assembled and packaged in ways that avoid stringent handling and shipping regulations.

SUMMARY OF THE INVENTION

In accordance with the invention, a device for producing an aqueous chlorine dioxide solution when exposed to water is provided. The device comprises a membrane shell defining a compartment which includes one or more dry chemical components capable of producing chlorine dioxide gas when exposed to water. Wick means are connected to the membrane shell and extend into the compartment for absorbing water and transporting water into the compartment whereby when the device is exposed to water the wick member absorbs water and transports water into the compartment, the chemical component(s) dissolve in the water and produce chlorine dioxide gas in the compartment, and chlorine dioxide gas exits the compartment through the membrane shell.

In a preferred embodiment, the compartment of the device includes a metal chlorite component and an acid component. In use, for example, the device is submersed in a container of water. The wick means quickly absorbs water and transports the water into the compartment. Metal chlorite and acid in the compartment then dissolve in the water and react to produce chlorine dioxide gas in the compartment. The chlorine dioxide gas passes through the membrane shell and transforms the water in the container into a chlorine dioxide solution. The solution can be used, for example, to disinfect surfaces or for a variety of other purposes as known in the art.

In one embodiment, the membrane shell is substantially impervious to liquid (e.g., water) but permeable to gas (e.g., chlorine dioxide gas). In another embodiment, the membrane shell is permeable to both liquid (e.g., water) and gas (e.g., chlorine dioxide gas).

In another embodiment, the wick means is a wick member having a first end that extends into the compartment and an opposing second end that extends beyond the outer edge of the membrane shell. In yet another embodiment, the wick means is a wick member that divides the compartment into first and second compartment sections. For example, the first compartment section can contain exclusively the metal chlorite component and the second compartment section can contain exclusively the acid component. This helps prevent the metal chlorite component and acid component from prematurely reacting. For example, in the event that a small amount of moisture accumulates in the device, the wick member will prevent a reaction that might otherwise occur. In another embodiment, the wick means is a wick member that divides the compartment into a plurality of compartment sections. For example, the metal chlorite component can be isolated in one compartment section, the acid component can be isolated in a second compartment section, and a surfactant or some other additive can be isolated in a third compartment section. In another embodiment, the wick means comprises at least two wick members, the wick members dividing the compartment into at least two compartment sections.

The inventive device is very useful for relatively small applications, for example where expensive chlorine dioxide generation equipment is not economically feasible.

An important advantage of the inventive device is that it can be modified to meet applicable shipping and handling regulations. For example, in one embodiment, the device is packaged to include a metal chlorite component together with any additives employed for the particular application. The compartment of the device includes a sealable opening therein for allowing the acid component to be placed in the compartment at the point of use (e.g., just prior to submersing the device to water). The acid component is separately packaged with the device; for example, it can be in tablet form. Prior to placing the device in water, the user merely inserts the acid in the device and seals the opening. By packaging the acid component separately, inadvertent premature exposure of the device to water (even a substantial amount of water) will not cause the chemicals to react. As a result, less stringent regulations regarding shipping and handling the device may apply.

If necessary or desirable for the end-use application, a weight can be attached to one of the membrane shell and the wick means (e.g., placed into the compartment) or otherwise incorporated into the device (e.g., formed as part of the wick member) to ensure that the device is immersed when it is placed in a body of water. Although it is not critical to do so, the device can also be packaged in a water-resistant envelope (e.g., a foil pouch) in order to minimize the risk of the device being inadvertently exposed to water prior to use. Also, for particular applications, the membrane shell can include a plurality of small openings for facilitating the passage of liquid (e.g., water) into and out of the device and decreasing the time required for the chlorine dioxide solution to be produced.

It is, therefore, an object of the present invention to provide a device that effectively produces an aqueous chlorine dioxide solution when exposed to water but has a stable shelf-life prior to exposure to water.

It is also an object of the present invention to provide such a device that is not susceptable to activation by ambient moisture.

It is a further object of the present invention to provide such a device that is less costly to produce and manufacture than other devices for producing aqueous chlorine dioxide solutions presently on the market.

It is yet another object of the present invention to provide a device that produces an aqueous chlorine dioxide solution in a relatively short amount of time when compared to prior art devices.

Still another object of the invention is to provide such a device that can be modified to meet applicable shipping and handling regulations.

Additional objects, features and advantages of the present invention will be readily apparent to those skilled in the art upon a reading of the detailed description of preferred embodiments of the invention which follows when taken in conjunction with the accompanying drawings.

BRIEF DESCRIPTION OF THE SEVERAL VIEWS OF THE DRAWING

FIG. 7 is a front elevational view of the device shown by FIGS. 4–6 as modified to include a plurality of openings in the outer membrane shell;

FIG. 8 is a front elevational view of yet another embodiment of the inventive device;

FIG. 9 is a cross-sectional view taken along line 9—9 of FIG. 8;

FIG. 10 is a cross-sectional view similar to the view shown by FIG. 9 but illustrating yet another embodiment of the inventive device;

FIG. 20 is a front elevation view of yet another embodiment of the inventive device;

FIG. 21 is a cross-sectional view taken along line 21—21 of FIG. 18;

DETAILED DESCRIPTION OF THE PREFERRED EMBODIMENTS OF THE INVENTION

Figure 1:
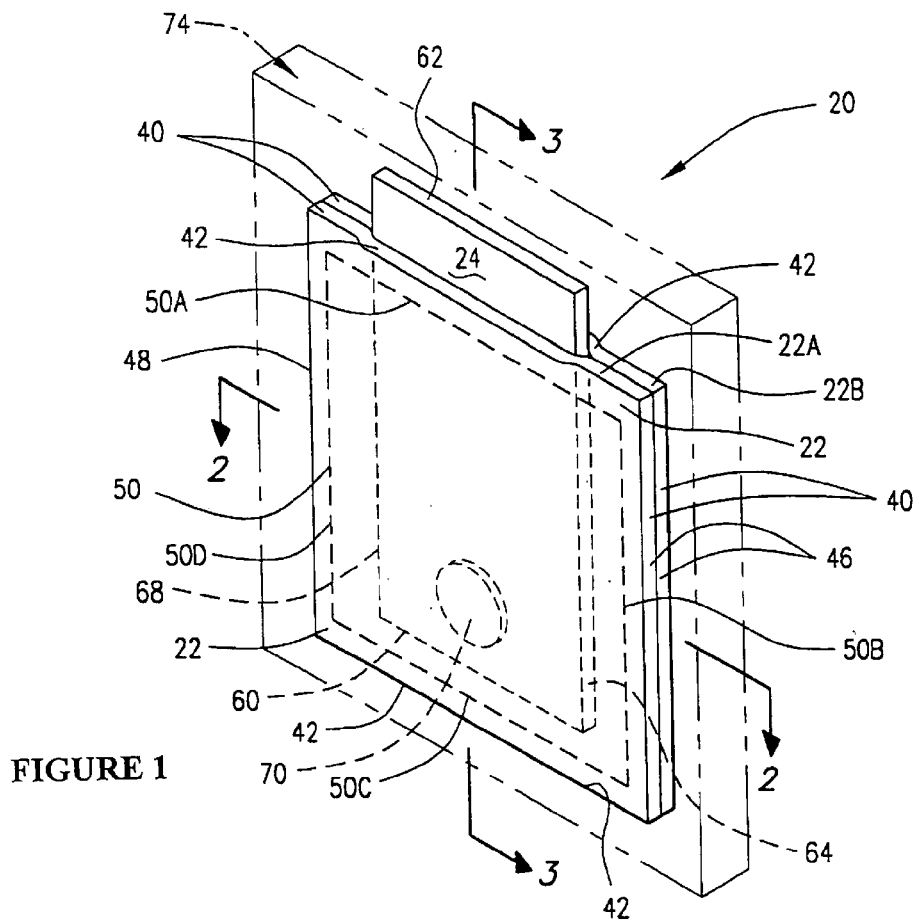
FIG. 1 is a front perspective view of one embodiment of the inventive device.
Figure 2:
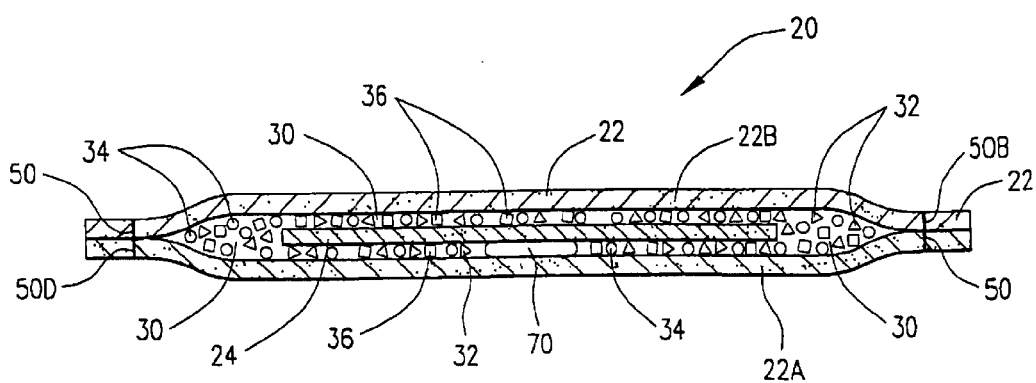
FIG. 2 is a cross-sectional view taken along line 2—2 of FIG. 1.
Figure 3:
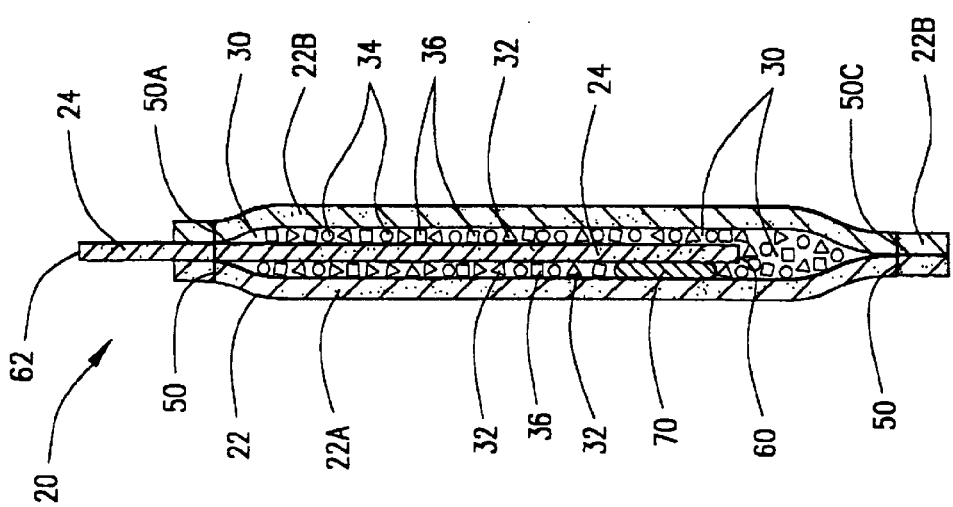
FIG. 3 is a cross-sectional view taken along line 3—3 of FIG. 1.

Referring now to the drawings and particularly to FIGS. 1–3, a first embodiment of the inventive device for producing an aqueous chlorine dioxide solution when the device is exposed to water is illustrated and generally designated by the numeral 20. As used herein, the term aqueous chlorine dioxide solution shall encompass both solutions containing chlorine dioxide and solutions containing acidified chlorite.

The device 20 comprises a membrane shell 22 and a wick member 24. The membrane shell defines a compartment 30 which includes one or more dry chemical components capable of producing chlorine dioxide gas when the device is exposed to water (i.e., contacted with sufficient water to cause the device to produce chlorine dioxide in its intended manner). The device is preferably exposed to water by placing or submersing it in a container of water.

The dry chemical components capable of producing chlorine dioxide gas upon exposure to water are preferably a metal chlorite component 32 and an acid component 34. Additives such as a catalyst for enhancing the reaction of the metal chlorite and acid, generally designated by the reference numeral 36, can also be included in the compartment 30. As used herein and in the intended claims, the term "dry chemical components" means chemical components in stable, solid, substantially anhydrous form.

The wick member 24 is connected to the membrane shell 22 and extends into the compartment 30. The wick member 24 functions as a wick in that it rapidly absorbs water from outside the device and transports the absorbed water into the compartment 30. For example, metal chlorite, acid and/or other chemicals in the compartment 30 dissolve in the absorbed water and react to produce chlorine dioxide gas. The chlorine dioxide gas efficiently exits the compartment 30 through the membrane shell 22 and possibly, to some extent, through the wick member 24.

The wick member 24 can be connected to the membrane shell 22 by being directly or indirectly fastened to a portion of the shell or by being merely inserted into the compartment 30. Due to a difference in the pressure outside the device 20 and the pressure in the compartment 30, the wick member 24 transports water into the compartment at a much faster rate than it allows water and/or solution to escape the device.

As shown by FIGS. 1–3, the membrane shell 22 is defined by two square panels 22A and 22B sealed together such that the compartment 30 is formed between the panels. The panels 22A and 22B are approximately the same size and form an outer edge 40 of the membrane shell 22. The outer edge 40 of the membrane shell 22 includes a top edge 42, bottom edge 44, side edge 46 and side edge 48. The panels 22A and 22B are sealed together along a line 50 which extends around the periphery of the panels just inside of the outer edge 40 of the membrane shell 22. Specifically, the seal extends along the line 50A adjacent to the top edge 42, along the line 50B adjacent to the side edge 46, along the line 50C adjacent to the bottom edge 44, and along the line 50D adjacent to the side edge 48 of the outer edge 40 of the membrane shell 22.

The panels 22A and 22B can be sealed together by a variety of means including stitching, heating and gluing. Preferably, the panels 22A and 22B are sealed together by stitching.

As shown, the wick member 24 is a rectangular sheet positioned between the panels 22A and 22B. The wick member 24 includes a bottom end 60 positioned in the compartment 30, an opposing top end 62 extending beyond the outer edge 40 of the membrane shell 22, and a first side 64 and second side 66 connecting the top and bottom ends and completing an outer periphery 68 of the wick member. Preferably at least 15% of the outer periphery of the wick member 24 extends beyond the outer periphery of the membrane shell 22.

In the embodiment shown by FIGS. 1–3, the wick member 24 is sealed between the panels 22A and 22B only along the line 50A adjacent the top end 62 of the wick member. This allows the various chemicals in the compartment 30 to commingle.

A weight 70 is inserted in the compartment 30 to ensure that the device sinks or is otherwise immersed when placed in a body of water. The weight can be attached to the device by other means as well; e.g., it can be attached to or formed as part of the membrane shell 22 and/or wick member 24. The size and shape of the weight 70 can vary depending on the size of the device 20 in general, the intended application and manufacturing and packaging concerns. The weight 70 can be formed of a variety of materials. It is important for the particular material used, however, to be inert with respect to the chemicals in the device. Preferably, the weight is formed of stainless steel.

In order to reduce the chance of a premature exposure of the metal chlorite component 32, acid component 34, additive(s) 36 and/or other chemicals in the compartment 30 to water, the membrane shell 22 and the wick member 24 can optionally be enclosed and sealed in a water-resistant package 74. The package 74 can be formed of a variety of materials. Preferably, the package 74 is a foil-laminated pouch.

The shape and size of the panels 22A and 22B and the corresponding compartment 30 can vary depending primarily on the amount of chemicals needed for the particular application (e.g., the amount of metal chlorite and acid needed for the desired amount and concentration of chlorine dioxide solution). Methods for calculating the amount of metal chlorite and acid needed to produce a given volume and concentration of chlorine dioxide solution are known to those skilled in the art. Additional factors affecting the size and shape of the panels 22A and 22B and the membrane shell 22 in general include the type of material used to form the panels, the intended application, packaging concerns and material compatibility. The panels 22A and 22B are preferably square or rectangular in shape in order to facilitate the step of fastening (e.g., stitching) the panels together.

The panels 22A and 22B and hence the membrane shell 22 are formed of a material and put together such that they function as a semi-permeable membrane. The membrane shell 22 (including the panels 22A and 22B) must be permeable to chlorine dioxide gas. Preferably, the membrane shell 22 is substantially impervious (most preferably completely impervious) to liquid (e.g., water). In this embodiment, water enters the device and solution exits the device only by way of the wick member 24. Chlorine dioxide gas generated by, for example, the reaction of chlorite ions and acid in the compartment 30 exits the device through the membrane shell 22 (i.e., the panels 22A and 22B) and possibly, to some extent, the wick member 24. The aqueous solution formed in the device is confined, for the most part, to the device. By preventing the aqueous solution formed and associated dissolved or solid chemicals from escaping the device through the membrane shell 22, the reaction is more complete and can be more easily controlled. Such a setup is desirable in applications wherein the amount of chlorine dioxide generated is critical and needs to be precisely controlled. For example, small amounts of water inadvertently encountered by the device will not enter the compartment 30 and cause premature reaction of the chemicals therein (a small amount of water is merely absorbed and held by the wick member 24).

In another embodiment, the membrane shell 22 is permeable to liquid (e.g., water and chlorine dioxide solution) and gas (e.g., chlorine dioxide gas). In this embodiment, water can enter the device and aqueous solution that is formed in the device can exit the device by way of the membrane shell 22. This decreases the amount of time required for the desired chlorine dioxide solution to be generated and is desirable in applications wherein the level of activation is low and immediate use of the solution is desired.

The permeability of the panels 22A and 22B with respect to gas and/or water can be the same or not the same depending on the desired function of the device. For example, the panel 22A can allow water to pass into one side of the compartment 30 while the panel 22B does not allow water to pass into the compartment 30.

The selected permeability of the panels 22A and 22B and hence the membrane shell 22 with respect to gas (e.g., chlorine dioxide) and liquid (e.g., water) is initially a function of the material composite and can be modified by mechanically, chemically and/or structurally altering the material. For example, as described below, a plurality of small openings can be formed in one or both of the panels 22A and 22B to facilitate the passage of liquid into and out of the compartment 30. Also, one or both of the panels 22A and 22B can be coated with various materials to alter the permeability thereof.

The membrane shell 22 (including the panels 22A and 22B) can be made of any membrane material that allows the membrane shell to function as described above; e.g., that allows the membrane shell to be substantially impervious to water but permeable to chlorine dioxide gas. For example, the membrane shell 22 (including the panels 22A and 22B) can be made from fibers. The fibers can be hydrophilic, hydrophobic or any combination thereof The fibers can be naturally occurring and/or synthetic, and can be woven or non-woven. Additionally, the fibers may be coated or non-coated. For example, the fibers can be coated to seal the fibers to each other or to other materials such as in a laminate composite.

Suitable synthetic fibers for the membrane shell 22 include polyvinyl chloride, polyvinyl fluoride, polytetrafluoroethylene, polyvinylidene chloride, polyacrylics such as Orlon® polyvinyl acetate, polyethylvinyl acetate, non-soluble or soluble polyvinyl alcohol, polyolefins such as polyethylene and polypropylene, polyamides such as nylon, polyesters such as Dacron® or Kodel® polyurethanes, polystyrenes and the like.

Suitable water impervious materials for forming the membrane shell 22 include microporous non-woven hydrophobic polymer sheet materials including non-woven polyethylene (e.g., Tyvek® brand materials sold by E.I. Du Pont de Nemours & Co.), microporous non-woven polypropylene materials, expanded polytetrafluoroethylene (e.g., Gore-Tex® brand sold by W.L. Gore), and kraft paper (e.g., X-Crepe-N Grade 4502 sold by Oliver Products Co.). Suitable water-permeable membrane materials include gelatin, polyvinyl alcohol, cellulose, and cellulose derivatives such as hydroxypropyl methyl cellulose. Other water permeable and water impervious membrane materials suitable for use in forming the membrane shell 22 (including the panels 22A and 22B) are known to those skilled in the art and are included within the scope of the present invention.

The panels 22A and 22B and hence the membrane shell 22 in general are preferably formed of a polyolefin material such as polyethylene and polypropylene. Most preferably, the panels 22A and 22B and hence the membrane shell 22 in general are formed of a microporous non-woven polyethylene.

The shape and size of the wick member 24 can vary depending on the size of the compartment 30, the water absorption rate desired, the type of material used to form the wick member, the intended application, packaging concerns and material compatibility. In the embodiment shown in FIGS. 1–3, the wick member 24 is almost as wide and extends almost to the bottom of the compartment 30. Approximately $\frac{1}{7}^{th}$ of the length of the wick member 24 extends beyond the outer edge 40 of the membrane shell 22. These features allow the wick member 24 to absorb and transport a relatively large amount of water on a relatively rapid basis. In order to increase the surface area of the wick member 24 to be exposed to the water even further, for example, the bottom end 60 of the wick member can also extend beyond the outer edge 40 of the membrane shell 22. As long as the wick member 24 is not sealed to the panels 22A and 22B around all of its edges, commingling of the chemicals will occur, at least to some extent.

In an application where a relatively slow release of chlorine dioxide is desired, the wick member 24 can be formed of a material that has a relatively slower wicking rate such that water is transported more slowly into the compartment 30. Alternatively, the surface area of the wick member 24 extending outside of the device can be-decreased so as to slow down the water absorption rate. For example, the wick member can be a small cylindrical rope extending into the compartment 30.

The wick member 24 can be made out of a large variety of materials. For example, in the preferred embodiment, the wick member can be made of virtually any material capable of quickly absorbing water and transporting the absorbed water into the device. For example, the material used to form the wick member 24 may be made of synthetic fibers, naturally occurring fiber(s) (both modified and unmodified) or both. The fibers can include hydrophilic fibers, hydrophobic fibers or a combination of hydrophilic and hydrophobic fibers.

Examples of suitable natural fibers for the wick member 24 include cotton, Esparto grass, bagasse, hemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as Orlon®, polyvinyl acetate, polyethylvinyl acetate, non-soluble and soluble polyvinyl alcohols, polyolefins such as polyethylene and polypropylene, polyamides such as nylon, polyesters such as Dacron® and Kodel®, polyurethanes, polystyrenes and the like. In order to function as a wick, certain synthetic fibers may require some modification (e.g., formed into laminates, etc.). The desired wicking action can result form absorption of water, capillary action and/or other mechanisms.

The wick member 24 is preferably formed of one or more natural fibers. More preferably, the wick member 24 is selected from the group consisting of cotton and wood pulp. Most preferably, the wick member is formed of non-synthetic fibers of cotton.

As known to those skilled in the art, the specific type of metal chlorite component, acid component and additive(s) employed in connection with the inventive device 20 will vary depending on numerous factors including the intended application for the device, packaging concerns and material compatibility. The reaction of a metal chlorite with an acid to generate chlorine dioxide is well known.

As used herein, the term "metal chlorite component" means a compound which is a metal chlorite or which forms a metal chlorite when exposed to water and/or the acid component. The metal chlorite component generally comprises a metal chlorite selected from the group consisting of alkali metal chlorites, alkaline earth metal chlorites and mixtures thereof Preferably, the metal chlorite component is selected from the group consisting of sodium chlorite, potassium chlorite, barium chlorite, calcium chlorite, and magnesium chlorite, more preferably from the group consisting of sodium chlorite, calcium chlorite, potassium chlorite and mixtures thereof Most preferably, the metal chlorite component is sodium chlorite ($NaClO_2$), particularly dry technical grade sodium chlorite (containing about 80% by weight sodium chlorite and 20% by weight sodium chloride).

As used herein, the term "acid component" means a compound which is acidic or which produces an acidic environment in the presence of water sufficient to activate or react with the metal chlorite component such that chlorine dioxide is produced. For example, the acid component can include an organic acid, a mineral acid or mixtures thereof. It is preferably a dry solid hydrophilic compound which does not substantially react with the metal chlorite until the chemicals are dissolved in water. Examples of organic acids that can be used include citric acid, boric acid, lactic acid, tartaric acid, maleic acid, malic acid, glutaric acid, adipic acid, acetic acid, formic acid, sulfamic and mixtures thereof. Examples of mineral acids that can be used include sulfuric acid, hydrochloric acid, phosphoric acid and mixtures thereof Preferred mineral acids are those that are of food grade quality such as phosphoric anhydride and sulfuric anhydride. Alternatively, an acid precursor that produces an acid when exposed to water can be used. Examples of suitable acid precursors include water soluble organic acid anhydrides such as maleic anhydride, and water soluble acid salts such as calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, and mixtures thereof Additional water-soluble acid forming precursors are known to those skilled in the art.

Of the organic acids, citric acid is most preferred. Of the mineral acids, phosphoric acid is most preferred. Preferably, the acid component is an organic acid. Most preferably, due to its food grade status, cost and low toxicity, the acid component is food grade, anhydrous citric acid.

As understood by those skilled in the art, the amounts of metal chlorite and acid that should be placed in the component will vary depending on the size of the compartment 30, the concentration of chlorine dioxide in the solution desired and the desired pH of the final solution. Preferably, the ratio of acid to metal chlorite in the compartment 30 is in the range of from about 5:1 to about 1:100, more preferably in the range of from about 1:1 to about 1:10.

The types and amounts of additive or additives included in the compartment 30 will also vary depending on the intended application, the types of metal chlorite and acid used, packaging concerns and material compatibility. Examples of additives that can be employed include adhesives, thickeners, penetrating agents, stabilizers, surfactants, binders, organic solids, inorganic solids, catalysts and other components that enhance the ability of the device to produce chlorine dioxide when exposed to water.

A catalytic amount of a catalyst selected from the group consisting of a transition metal, a transition metal oxide and mixtures thereof can be included in the compartment 30 to speed up the reaction. The use of such catalysts is disclosed by U.S. Pat. No. 5,008,096, issued to Ringo on Apr. 16, 1991, which is incorporated by reference herein.

The metal chlorite component, acid component and any additive(s) utilized in connection with the device 20 can be in any physical form which can be contained within the device in dry form; e.g., powders, granules, pellets, tablets, agglomerates and the like. Preferably, the components are in powder form because powders tend to dissolve in water and react more quickly when compared to large particles such as pellets or agglomerates.

The metal chlorite and acid can each be impregnated on inert carriers that are chemically compatible with the components, e.g., zeolite, kaolin, mica, bentonite, sepiolite, diatomaceous earth, and synthetic silica. Other such carriers are known to those skilled in the art. For example, a carrier can be useful to control the release of the chlorite and acid into solution and thus control the reaction even further. Such a carrier is preferably insoluble in water.

The types of metal chlorites, acids and additives that can be employed and well as the amounts of components, reaction conditions and other involved parameters are described in Canadian Patent No. 959238 and PCT Application No. PCT/US98/22564, which are incorporated by reference herein.

Figure 4:
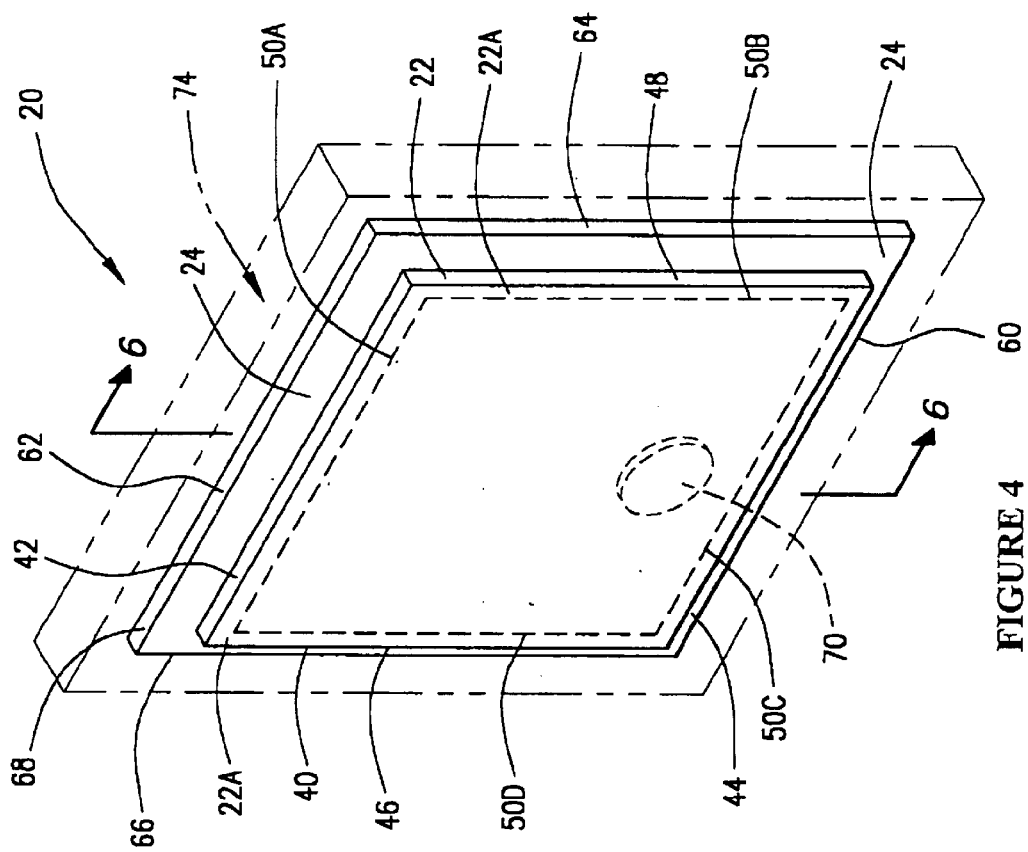
FIG. 4 is a front perspective view of another embodiment of the inventive device.
Figure 6:
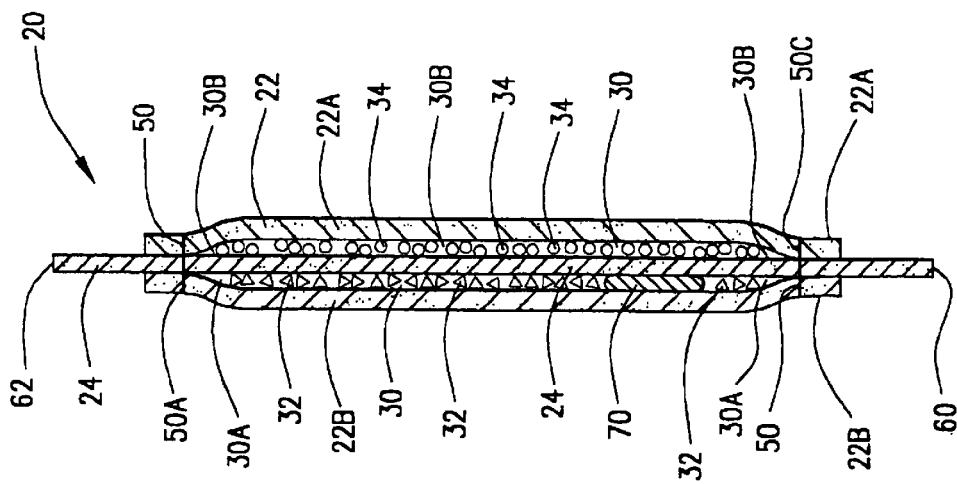
FIG. 6 is a cross-sectional view taken along line 6—6 of FIG. 4, or line 6—6 of FIG. 5.
Figure 5:
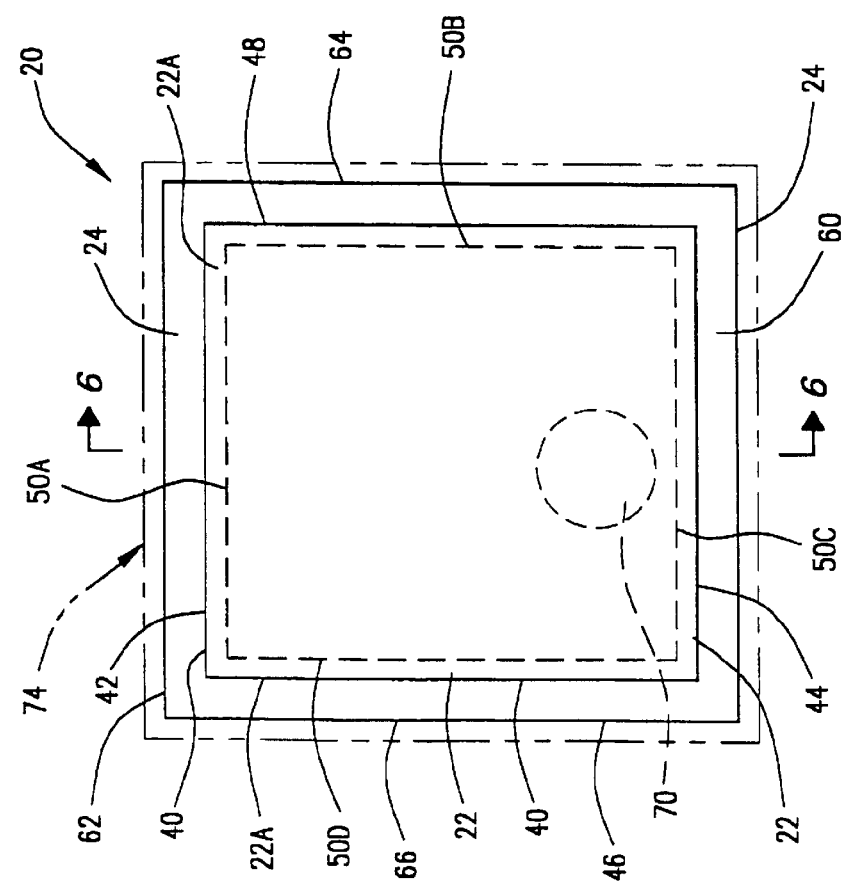
FIG. 5 is a front elevational view of the device shown by FIG. 4.

Referring now to FIGS. 4–6, a second embodiment of the inventive device 20 will be described. This embodiment of the device 20 is the same as the embodiment shown by FIGS. 1–3 and described above except for the size of the wick member 24 and the way that the wick member is fastened to the membrane shell 22.

In the embodiment shown by FIGS. 4–6, the wick member 24 is of a size such that the entire outer periphery 68, including the bottom end 60, top end 62, first side 64 and second side 66, of the wick member extends beyond the entire outer edge 40 of the membrane shell 22. The wick member 24 is sealed to the panels 22A and 22B of the membrane shell 22 along the entire line 50, that is continuously along line 50A, 50B, 50C, and 50D. Due to the fact that the entire outer periphery 68 of the wick member 24 extends beyond the outer periphery 40 of the membrane shell 22, the wick member 24 is able to absorb and transport water into the compartment at a faster rate. Due to the fact that it is sealed to the panels 22A and 22B of the membrane shell 22 along the entire line 50, the wick member 24 functions to divide the compartment 30 into a first compartment section 30A and a second compartment section 30B.

In the embodiment shown by FIGS. 4–6, the metal chlorite component is preferably contained exclusively in one compartment, say compartment section 30A, and the acid component is contained exclusively in the other compartment, say compartment section 30B (the additive(s) 36 can be placed in one or both compartment sections). The compartment division further prevents a premature reaction of metal chlorite and acid in the event of an inadvertent exposure to water prior to the intended use of the device. For example, when the device 20 is immersed in water in accordance with its intended use, the wick member 24 absorbs a relatively large amount of water and transports the water into the first and second compartment sections 30A and 30B such that metal chlorite in the first compartment section and acid in the second compartment section contact the water, dissolve in the water, traverse the wick divider, come into contact with one another and react to produce chlorine dioxide in the compartment 30. A small amount of water will not be sufficient to allow the components to traverse the wick divider and react. It is only when a substantial amount of water enters the device that the metal chlorite and acid component come into contact with one another to generate chlorine dioxide. A small amount of water vapor that may enter the device through the membrane shell 22 is absorbed by the chemicals.

The wick divider 24 gives the inventive device a longer shelf life than the shelf life of the prior art devices and allows the device to be produced in normal environments (as compared to low humidity environments required for production of prior art devices). Special moisture-resistant packaging is not required to protect against ambient moisture exposure.

Additional uses of the first and second compartment sections 30A and 30B of the embodiment shown by FIGS. 4–6 can be advantageously made to fit particular applications. For example, a mixture of the metal chlorite component and acid component can be placed in both compartment sections. This arrangement is advantageous in that the reaction occurs more quickly. Alternatively, a mixture of the metal chlorite component and acid component can be placed in one compartment section and one or more additives can be placed in the second compartment section. This arrangement might be advantageous in applications wherein the additive might prematurely react with the metal chlorite and acid.

The embodiment shown by FIG. 7 is the same as the embodiment shown by FIGS. 4–6 except the membrane shell 22 (including both the panel member 22A and the panel member 22B) includes a plurality of relatively small openings 80 (e.g., 50–500 microns in diameter) extending from the outside of the membrane shell into the first and second compartment sections 30A and 30B. The openings 80 facilitate the passage of liquid (e.g., water and aqueous solution of chlorine dioxide) into and out of the compartment 30. The openings 80 can further reduce the amount of time required for the desired aqueous chlorine dioxide solution to be generated. Each embodiment of the inventive device can include similar openings.

Referring now to FIGS. 8 and 9, another embodiment of the inventive device 20 is illustrated and will be described. The embodiment shown by FIGS. 8 and 9 is the same as the embodiment shown by FIGS. 4–6, except that an additional seal is made through the device along a line 50E which extends from the line 50B across the middle section of the device to the line 50C. The seal (e.g. formed by stitches) extends from the outside of the panel section 22B though the wick member 24 to the outside of the panel member 22A to effectively divide the compartment into four (4) compartment sections, 30A1, 30A2, 30B1 and 30B2. The plurality of compartments is useful for various applications. For example, as shown by FIG. 9, an acid component 34 can be placed in compartment section 30A1, a metal chlorite component 32 can be placed in compartment section 30B1, a first additive 36A can be placed in compartment section 30B2 and a second additive 36B can be placed in compartment section 30A2. This arrangement is useful in applications wherein the release of one or more additives requires special conditions. For example, if a surfactant needs more water to function than will be brought in by the wick member, small perforations can be made in the membrane shell over the section of the device containing the surfactant to allow more water to enter into this section of the device when the device is placed in water.

FIG. 10 illustrates an embodiment of the invention that is the same as the embodiment shown by FIGS. 8 and 9 except the that the seal made through the device along line 50E only extends from the outside of the panel section 22B to the wick member 24 thus creating a device having three compartment sections, 30A, 30B1 and 30B2. Again, the number of compartment sections can be varied to suit virtually any application.

Figures 11, 12:
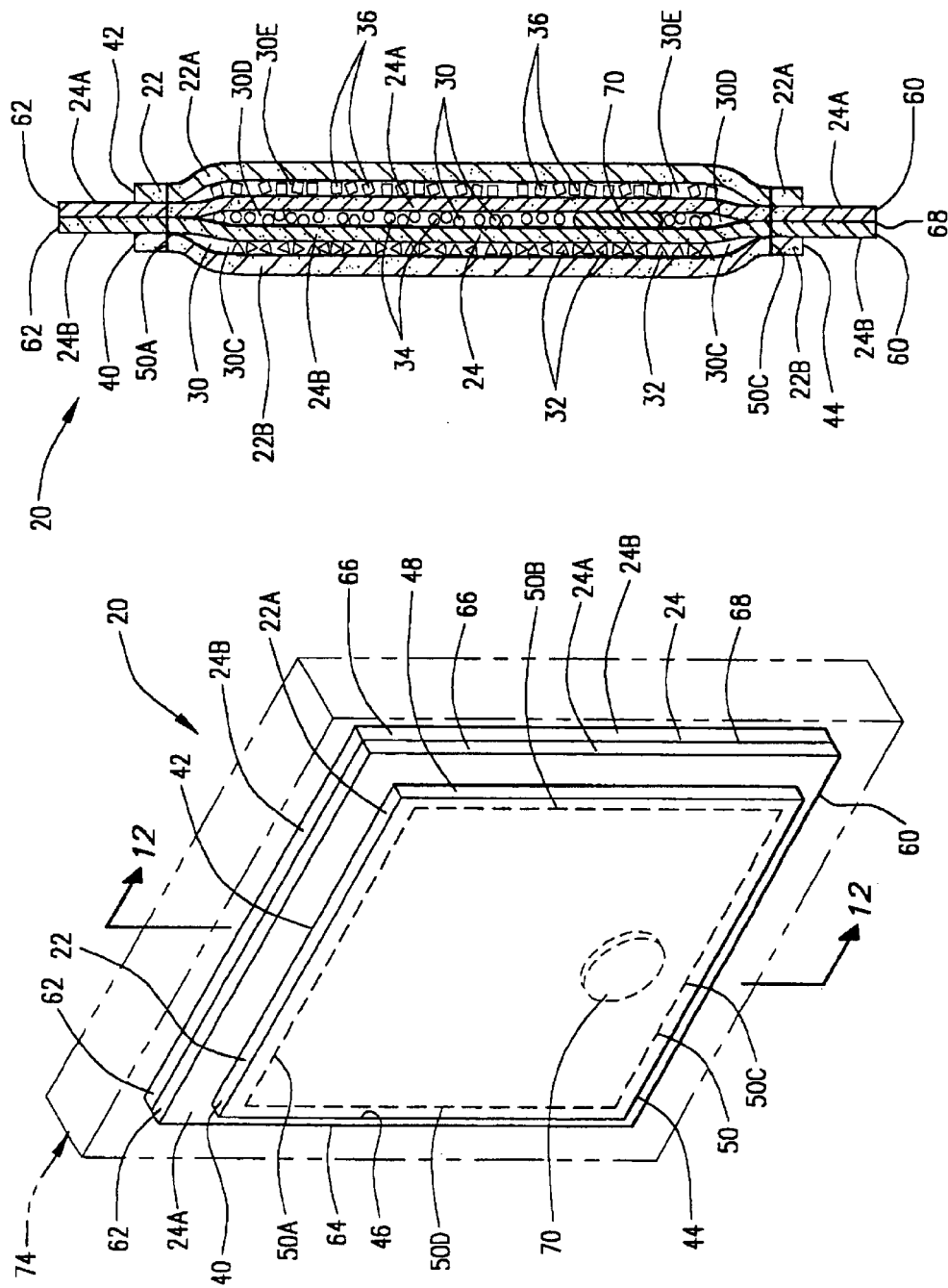
FIG. 11 is a front perspective view of yet another embodiment of the inventive device.
FIG. 12 is a cross-sectional view taken along line 12—12 of FIG. 11.

Referring now to FIGS. 11 and 12, yet another embodiment of the inventive device 20 is illustrated. This embodiment is the same as the embodiment shown by FIGS. 4–6 except that it includes two wick members 24, 24A and 24B. The wick members 24A and 24B are sealed together with two the panel members 22A and 22B along the entire line 50, that is continuously along the line 50A, 50B, 50C and 50D. The use of two wick members 24 increases the wicking ability of the device 20 resulting in faster absorption and transport of water into the compartment 30. The use of two wick members also makes it possible to divide the compartment 30 into a large number of compartment sections. As shown by FIGS. 11 and 12, the wick members 24A and 24B divide the compartment 30 into compartment sections 30C, 30D and 30E. If desired, the device can be sealed along its mid-section (as in the embodiments shown by FIGS. 8–10) to create, for example, 5, 6 or virtually any number of compartment sections.

FIGS. 13–23 illustrate certain embodiments of the inventive device 20 that are designed to accommodate government regulations and restrictions regarding shipping and handling of the device. For example, certain federal and state Department of Transportation regulations may prevent the device from being shipped in a way that would allow the acid and metal chlorite to come into contact with one another in the event of accidental exposure to water unless the package for the device includes a warning such as "DANGEROUS WHEN WET" and special handling and shipping requirements are met.

Figure 14:
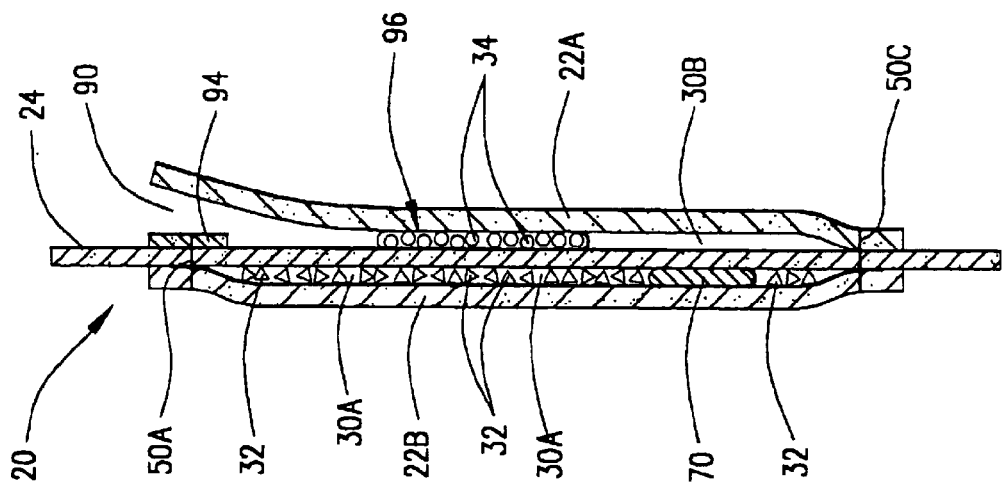
FIG. 14 is a cross-sectional view taken along line 14—14 of FIG. 13.
Figure 13:
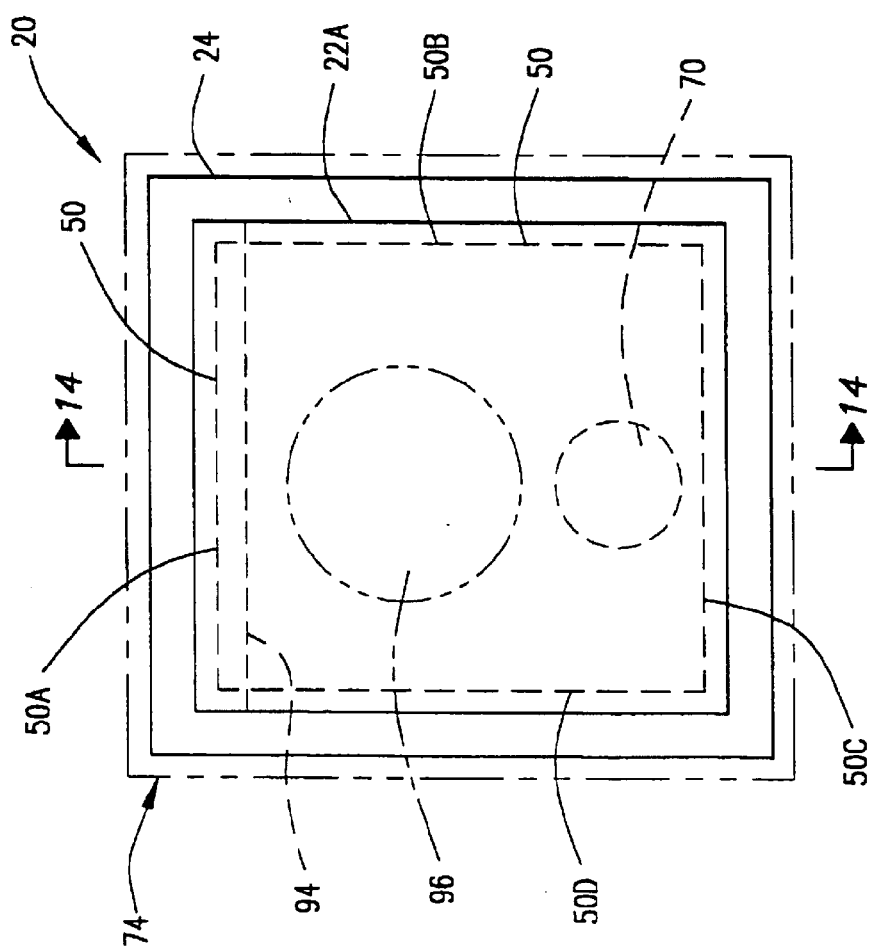
FIG. 13 is a front perspective view of yet another embodiment of the inventive device.
Figure 15:
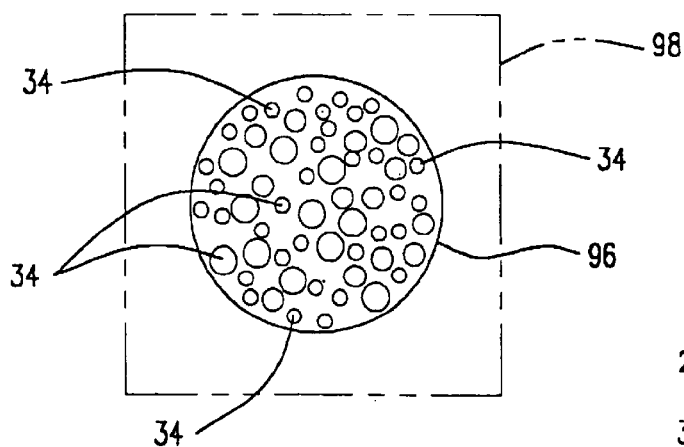
FIG. 15 is a front elevation view of a component of the device shown by FIGS. 13 and 14.

Referring now to FIGS. 13–15, a first embodiment of the inventive device 20 that is designed to accommodate government regulations and restrictions is illustrated. This embodiment of the inventive device 20 is the same as the embodiment shown by FIGS. 4–7 in all respects except that the first compartment section 30A includes the metal chlorite component 32, and the second compartment section 30B includes a sealable opening 90 therein. The metal chlorite component 32 is sealed in the compartment 30A by the seal extending along the entire line 50, that is continuously along lines 50A, 50B, 50C and 50D. The seal along line 50A, however, does not extend through the panel 22A of the membrane shell 22, leaving the opening 90 in the compartment 30B. An adhesive strip 94 extends along the top portion of the device and is sealed to the device along the line 50A.

The acid component 34 is not initially placed in the device. Rather, the acid component 34 is placed in a separate package 98 (FIG. 15) which can be included in the main package 74 for the device. This prevents the acid component 34 and metal chlorite 32 from coming into contact with one another in the case of accidental exposure of the device to water. In this embodiment, the acid component 34 is preferably in the form of a tablet 96. Alternatively, for example, the acid component 34 can be an acid powder wrapped in a material with wicking action, preferably the same material used to form the wick member 24. The acid is placed in the device with the wrapping thereon. This further delays the reaction between the metal chlorite and acid and provides additional reaction control, if necessary, when the device is placed in water. The separate package 98 can be formed of any water impervious material (e.g., laminated foil).

Although the adhesive strip 94 is preferred, any means for resealing the opening 90 can be used. For example, Velcro®, buttons, clamps, staples, zippers or other sealing means can be used.

At the point of use, the user merely removes the acid component 34 (e.g., the tablet 96) from the package 98 and inserts it into the second compartment section 30B through the opening 90 therein (FIG. 14 shows the device with the acid tablet 96 already inserted therein). The user then merely seals the device by pressing the top portion of the panel member 22A against the adhesive strip 94 (typically a protective paper coating must first be removed from the adhesive strip 94) and places the device in water (at this point the device functions in the same manner as the device shown by FIGS. 4–7). The user also has the option to add other components, e.g., one or more additives, additional weights, etc. just prior to use of the device. If desired, the acid component 34 and/or one or more additives 36 can be initially sealed in the first compartment section 30A and the metal chlorite component 32 can be separately packaged for insertion at the point of use.

Figure 18:
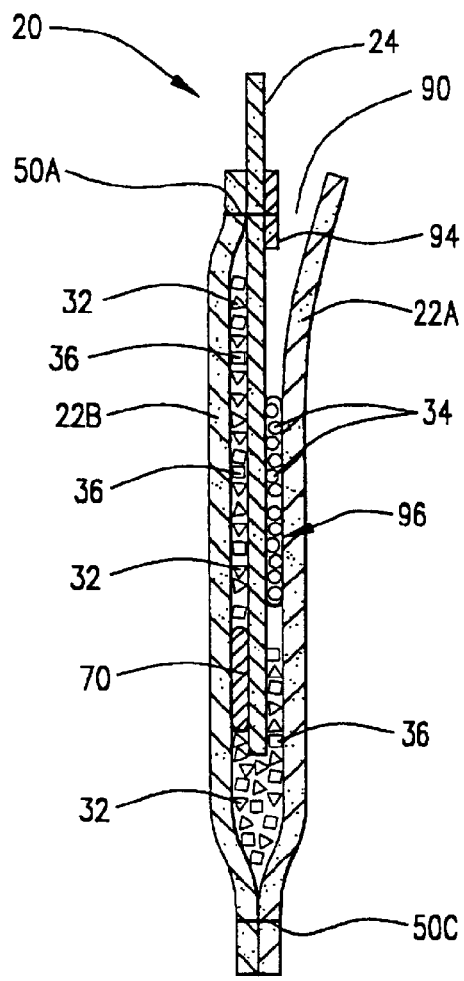
FIG. 18 is a view similar to the view shown by FIG. 14 except it shows another embodiment of the inventive device.

The same features (e.g., the opening 90 and adhesive strip 94) can be employed in connection with the other embodiments of the inventive device. For example, FIG. 18 illustrates an embodiment similar to the embodiment of the inventive device shown by FIGS. 1–3 (e.g., the wick member is not sealed on all sides allowing the chemicals to commingle) except it includes the opening 90, adhesive strip 94, etc.).

Figure 16:
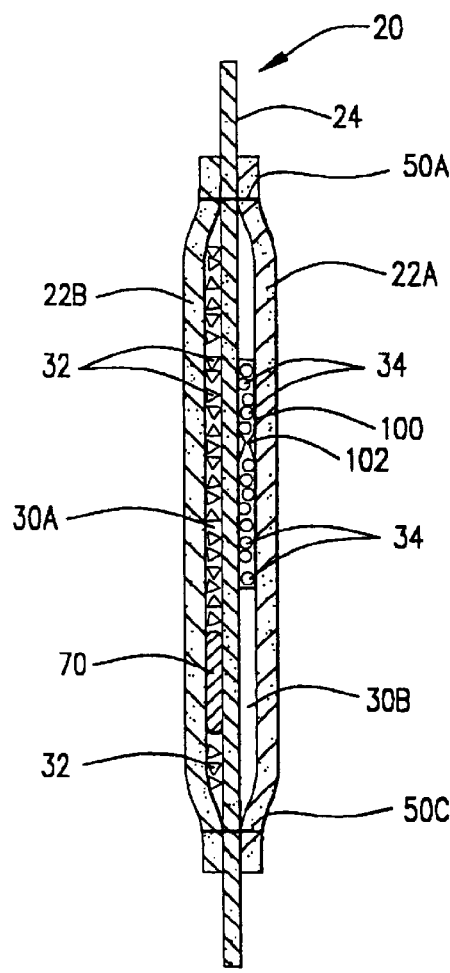
FIG. 16 is a front elevation view of a component of yet another embodiment of the inventive device.
Figure 17:
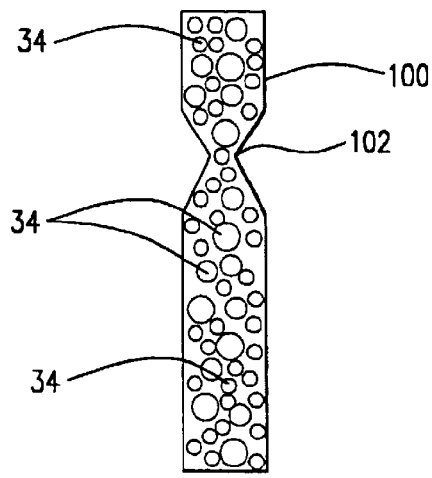
FIG. 17 is a cross-sectional view similar to the view shown by FIG. 14 except it shows the embodiment of the inventive device to which FIG. 16 relates.
Figure 19:
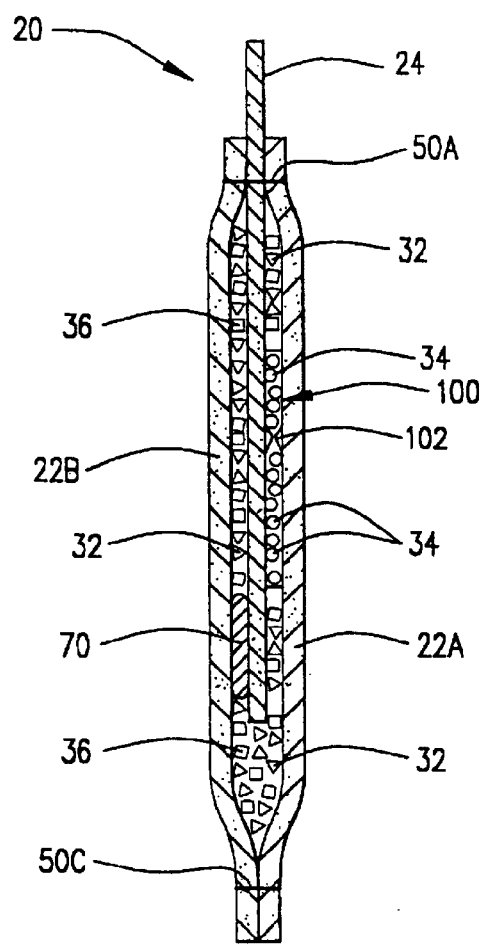
FIG. 19 is a view similar to the view shown by FIG. 17 except is shows yet another embodiment of the inventive device.
Figures 22, 23:
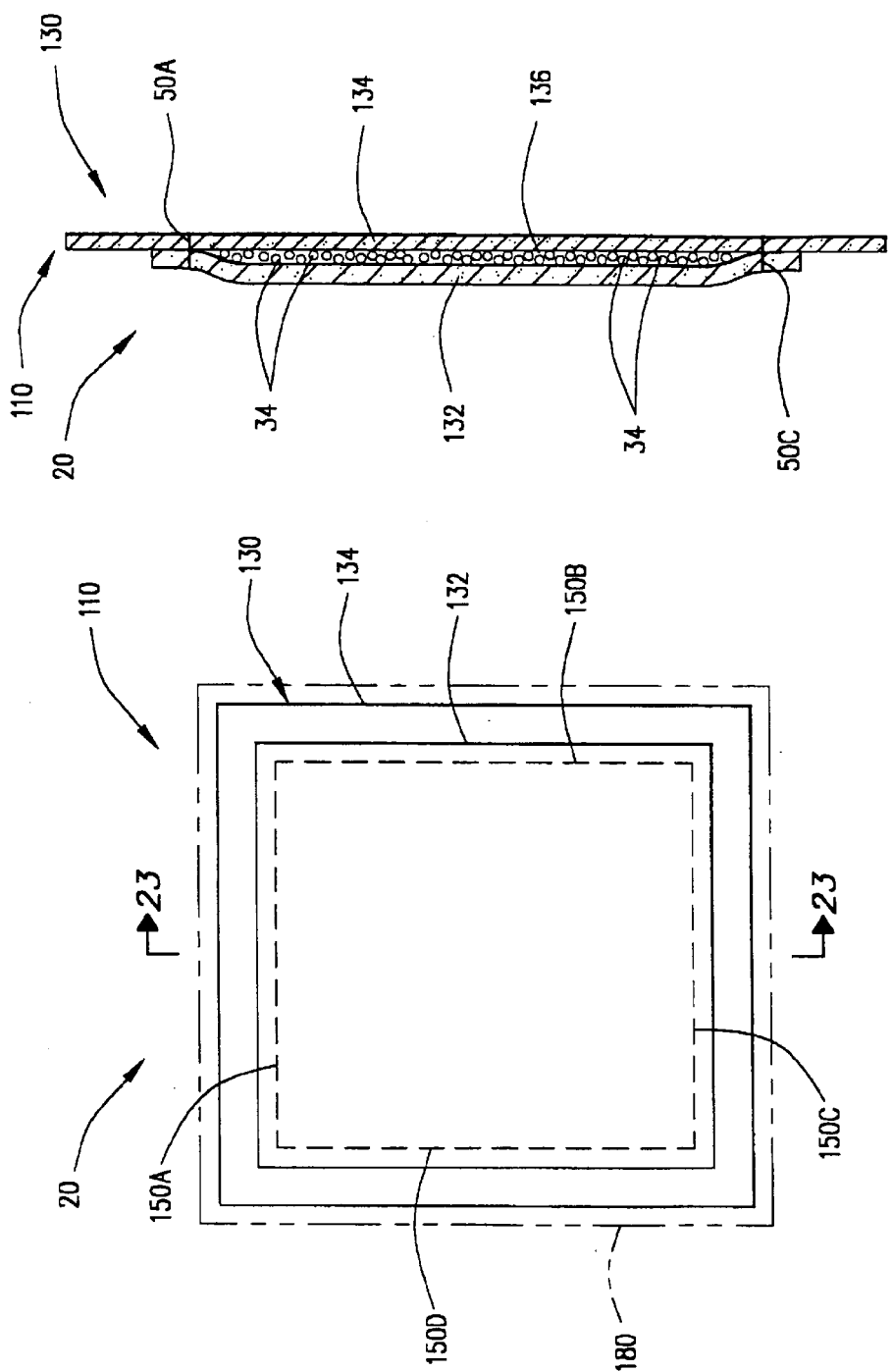
FIG. 22 is a rear elevation view of the embodiment of the inventive device shown by FIGS. 20 and 21.
FIG. 23 is a cross-sectional view taken along line 23—23 of FIG. 22.

FIGS. 16, 17 and 19 illustrate a second embodiment of the inventive device 20 that is designed to accommodate government regulations and restrictions regarding shipping and handling of the device. In this embodiment, the device 20 further comprises a manually openable ampule 100. The ampule 100 is positioned in the second compartment section 30B and contains the acid component 34. The ampule 100 is impervious to water and thereby prevents the acid component 34 from coming into contact with the metal chlorite component 32 until the ampule is manually opened. Alternatively the ampule 100 can be positioned in the first compartment section 30A and contain the metal chlorite component 32.

The ampule 100 is merely a safety device—it prevents the acid component 34 from contacting the metal chlorite component 32 and/or other chemicals in the compartment 30 in the event the device is prematurely exposed to or even immersed in water. The device 20 is assembled with the ampule 100 sealed therein. At the point of use, prior to placing the device 20 in water, the user merely manipulates the device 20 to break the ampule 100 such that the acid component 34 is released therefrom into the compartment 30B. The device 20 then functions in its intended manner, e.g., in the same manner in which the embodiment of the device 20 shown by FIGS. 4–7 functions.

The ampule 100 can be made out of any water and acid impervious material. For example, the ampule 100 can be made out of polyvinyl chloride, glass or plastic. The ampule 100 is designed such that simple hand pressure can break the ampule open. For example, as shown by FIG. 16, the ampule 100 can include a weak point 102 which allows the ampule 100 to be easily broken open by the user.

Again, the same features (e.g., the ampule 100) can be employed in connection with all of the embodiments of the inventive device 20. For example, FIG. 19 illustrates use of ampule 100 in connection with the embodiment of the inventive device 20 shown by FIGS. 1–3; i.e., the acid component 34 is contained in the ampule 100 which is in turn sealed within the compartment section 30B. Inasmuch as the ampule contains the acid, this embodiment of the device functions similarly to the embodiment of the device shown by FIGS. 4–6 in that the metal chlorite component and acid component are not allowed to commingle prior to use of the device.

Referring now to FIGS. 20–23, yet another embodiment of the inventive device 20 designed to accommodate government regulations and restrictions regarding shipping and handling of the device is illustrated. This embodiment of the device consists of a kit 110 which allows the user to complete assembly of the device 20 at the point of use. The kit 110 includes a first chemical unit 112, a second chemical unit 130 and attachment means, such as an adhesive strip 140, attached to one of the first chemical unit and the second chemical unit for allowing the units to be attached together to assemble the device.

The first chemical unit 112 includes a first membrane shell 114 and a first wick member 116 connected to the first membrane shell and forming a first compartment section 118 between the first membrane shell and the first wick member. The first compartment section 118 contains the metal chlorite component 32. The first wick member 116 is capable of absorbing water and transporting water into the first compartment section 118. The first membrane shell 114 and first wick member 116 are sealed together along a line 150 (i.e., along lines 150A, 150B, 150C and 150D). A weight 170 is included in the first compartment section 118 for causing the assembled device to submerge when placed in water by the user.

The second chemical unit 130 includes a second membrane shell 132, a second wick member 134 connected to the second membrane shell and forming a second compartment section 136 between the second membrane shell and the second wick member. The second compartment section 136 contains the acid component 34. The second wick member 134 is also capable of absorbing water and transporting water into the second compartment section. The second membrane shell 132 and second wick member 134 are sealed together along a line 150 (i.e., along lines 150A, 150B, 150C and 150D).

An adhesive strip 140 is attached to the first wick member 116 of the first chemical unit 112 adjacent to the outer edge of the first wick member. The adhesive strip 140 allows the first chemical unit 112 and second chemical unit 130 to be attached together at the point of use. It is desirable that the adhesive strip 140 be as close to the outer edge of the wick member 116 as possible so as to not inhibit the flow of water and dissolved materials in and out of the compartments 118 and 136.

Except for the chemicals they contain and the adhesive strip 140 on the first chemical unit 112, the first chemical unit and second chemical unit 130 are essentially identical. Each unit is placed in an envelope 180 and placed in single package for shipment.

At the point of use, the user merely removes the first chemical unit 112, and second chemical unit 130 from their individual packages 180, removes the paper cover from or otherwise activates the adhesive strip 140 and sticks the two units together such that the first wick member 116 and second wick member 134 are in alignment and facing one another. The user then inserts the device in water (at this point the device functions in essentially the same manner as the device shown by FIGS. 4–7).

Although the adhesive strip 140 is preferred, any means for connecting the first chemical unit 112 and second chemical unit 130 together can be employed. For example, Velcro®, buttons, snaps, clamps or other attachment means can be used.

Production of the Inventive Device 20

Each embodiment of the inventive device 20, including the components of the kit 110, can be produced using a variety of methods. For example, in one method of producing the embodiments of the device 20 shown by FIGS. 1–7, the wick member 24 is placed between the panels 22A and 22B forming the membrane shell 22. In order to produce a device such as the device shown by FIGS. 4–6, the entire outer periphery 68 of the wick member 24 extends beyond the outer periphery 40 of the membrane shell 22. The panels 22A and 22B and wick member 24 are then sealed just inside the outer periphery 40 of the panels such that only a small opening allowing access to the compartment 30 between the panels remains. The metal chlorite composition and acid composition is then placed into the appropriate compartment section and the opening allowing access to the compartment 30 is sealed to completely enclose the compartment 30 as well as the compartment sections therein.

The panels 22A and 22B and wick member 24 can be sealed together by a variety of means such as gluing, heat sealing, pressure sealing, stapling or sewing. Preferably, the panels 22A and 22B are heat sealed to the wick member 24.

In producing the device illustrated by FIGS. 11 and 12, a panel 22A is placed on top of a corresponding wick member 24 and sealed just inside the outer periphery 40 of the panel 22A such that only a small opening remains for access to the compartment between the panel and the wick member. The metal chlorite component is then placed into the compartment and the opening allowing access to the compartment is sealed. The process is then repeated to create an identical arrangement containing the acid component. The two pouches are then placed together at the wick member surfaces and sealed together.

The embodiments of the device shown by FIGS. 13–23 can be produced in a similar fashion.

For example, in the embodiment shown by FIGS. 4–6 of the drawings, the panels 22A and 22B forming the membrane shell 22 are formed of a non-woven polyethylene material (Tyvek® brand sold by Du Pont). The wick divider 24 is made out of non-synthetic cotton fiber (e.g., Scott® paper towel). Approximately 0.5 grams of citric acid are contained in the first compartment section 38. Approximately 0.5 grams of sodium chlorite are contained in the second compartment section 30B. The device 20 is then immersed in approximately 1 liter of water to produce an aqueous solution containing approximately 100 ppm of chlorine dioxide. This solution can be used as a disinfectant or for a variety of other purposes.

Operation of the Inventive Device 20

In use, an embodiment of the inventive device 20, as described above, is first selected for the particular application involved (taking into account applicable shipping and handling regulations). The amount and concentration of chlorine dioxide solution to be generated is considered with respect to the amounts of the metal chlorite component, acid component and other chemicals utilized and the size of the device selected.

Generally, chlorine dioxide solutions useful as antimicrobial agents have a chlorine dioxide concentration of from about 0.1 ppm to about 1000 ppm. Therefore, one liter of a 50 ppm solution can be prepared by dissolving 0.5 grams of sodium chlorite in water. The amount of acid needed can be calculated accordingly. However, the acid is usually present in stoichiometric excess to ensure that the reaction goes to completion and the maximum amount of chlorine dioxide is generated from the metal chlorite. Therefore, the amount of acid should be sufficient to provide an excess of acid beyond that needed to neutralize the alkalinity of the metal chlorite in the water. Preferably, the amount of acid should be sufficient to maintain the pH below 5, preferably below 3, when in contact with the metal chlorite.

Figure 24:
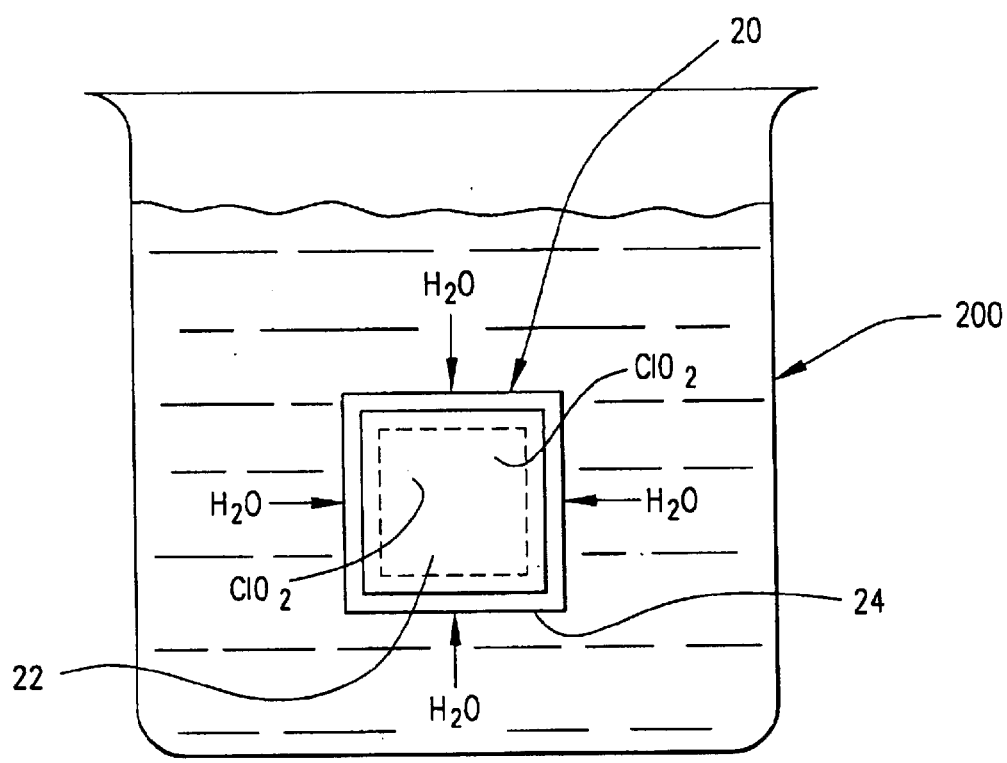
FIG. 24 is a front elevation view of a container of water having the inventive device submersed therein.

The device 20 is then contacted with (e.g., immersed in) a container 200 of water. As shown by FIG. 24, water is absorbed by the wick member 24 (or wick members 116 and 134) and transported by the wick member(s) into the compartment 30 or compartment sections 30A, 30B, 118, 136, etc. Metal chlorite and acid in the compartment or compartment sections then dissolve in the water and react to produce chlorine dioxide gas. If the metal chlorite, acid and other chemicals are separated by the wick member and contained in individual compartments, the chemicals individually dissolve in the water and the various aqueous solutions formed traverse the wick divider and commingle. Commingling of the solutions results in the reaction of the chemicals and the production of chlorine dioxide gas. The chlorine dioxide gas then exits the device through the membrane shell 22 and possibly, to some extent, the wick divider and transforms the surrounding water into an aqueous chlorine dioxide or acidified sodium chlorite solution. Some of the aqueous solution formed in the device may also enter the container of water through the wick member where the components may also react to produce additional chlorine gas.

Depending on the material used to form the membrane shell, water may also enter the device and aqueous solution may also exit the device through the membrane shell.

Thus, the present invention has many advantages over the prior art. The wick member (or members) carries out many important functions. First, it absorbs water and transports the water into the compartment(s) in the device in a controlled manner. The wick member (or members) greatly decreases the time required for water to get into the device yet keeps the chemicals in the device from prematurely reacting. The size, shape and number of compartments within the inventive device can be easily varied to fit virtually any application.

The embodiments of the device shown by FIGS. 13–23 allow the device to be easily packaged, shipped and handled providing the device with a tremendous advantage over the prior art devices used heretofore.

The following examples are provided to further illustrate the effectiveness of the inventive device.

EXAMPLE 1

A microporous, hydrophobic non-woven polyethylene sheet material (Tyvek® brand sold by E.I. Du Pont de Nemours & Co.—type 1059B) was cut and sealed with a heat-sealing device to make a single compartment pouch approximately 1 inch by 2 inches. The pouch was filled with a mixture of 0.5 grams powdered technical grade sodium chlorite and 0.5 grams powdered citric acid. The pouch was then heat sealed and placed into 500 mL tap water at a temperature of 75° F. The concentration of chlorine dioxide gas in the solution was measured with a spectrophotometer by recording the absorbance of the solution at 360 nm and using a molar absorptivity of 1,100 liters per mole-cm. Measurements were taken at five-minute intervals for 25 minutes. The results are shown in Table 1.

TABLE 1

| Time | Concentration |
|---|---|
| 5 minutes | 2.1 ppm |
| 10 minutes | 5.2 ppm |
| 15 minutes | 8.5 ppm |
| 20 minutes | 11.3 ppm |
| 25 minutes | 16.5 ppm |

The results show by Table 1 demonstrate that in the absence of a wick member, chlorine dioxide solutions are produced relatively slowly, e.g., it took approximately 25 minutes to produce a 16.5 ppm chlorine dioxide solution.

EXAMPLE 2

A microporous, hydrophobic non-woven polyethylene sheet material (Tyvek® brand sold by E.I. Du Pont de Nemours & Co.—type 1059B) was cut and sealed with a heat-sealing device to make a single compartment pouch approximately 1 inch by 2 inches. The pouch was then penetrated using a sewing needle so that approximately 30 holes about the size of the end of the needle (i.e., 0.05 mm) were made in the pouch. The pouch was filled with a mixture of 0.5 grams powdered technical grade sodium chlorite and 0.5 grams powdered citric acid. The pouch was then heat sealed and placed into 500 mL tap water at a temperature of 75° F. The concentration of chlorine dioxide gas was measured with a spectrophotometer by recording the absorbance of the solution at 360 nm and using a molar absorptivity of 1,100 liter per mole-cm. Measurements were taken at five-minute intervals for 20 minutes. The results are shown in Table 2.

TABLE 2

| Time | Concentration |
|---|---|
| 5 min. | 3.0 ppm |
| 10 min. | 12.2 ppm |
| 15 min. | 28.1 ppm |
| 20 min. | 29.3 ppm |

Table 2 demonstrates that the small perforations in the device allowed the water to enter the device more quickly and resulted is a faster production rate for the chlorine dioxide solution, e.g., it took 20 minutes to produce a 29.3 ppm solution.

EXAMPLE 3

The device of the present invention, in a form such as the embodiment shown by FIGS. 4–6, was constructed and compared to the prior art devices shown in Examples 1 and 2. The membrane shell (the panels 22A and 22B) was made of a microporous, hydrophobic non-woven polyethylene sheet material (Tyvek® brand sold by E.I. Du Pont de Nemours & Co.—type 1059B). The wick member 24 was made of Scott® brand "Ultrawipes" paper towel.

The membrane shell material and wick member were cut and sealed with a heat-sealing device to make the device (including first and second compartment sections) which was approximately 1 inch by 2 inches. The first compartment section was filled with 0.5 grams powdered technical grade sodium chlorite and the second compartment section was filled with 0.5 grams powdered citric acid. The pouch was then heat sealed and placed into 500 mL tap water at a temperature of 75° F. The concentration of chlorine dioxide gas was measured with a spectrophotometer by recording the absorbance of the solution at 360 nm and using a molar absorptivity of 1,100 liter per mole-cm. Measurements were taken at five-minute intervals for 15 minutes. The results are shown in Table 3.

TABLE 3

| Time | Concentration |
|---|---|
| 5 min. | 31.1 ppm |
| 10 min. | 39.7 ppm |
| 15 min. | 50.0 ppm |

Table 3 clearly shows that the device of the present invention produces chlorine dioxide solutions much more quickly than those of the prior art, e.g., it took only 15 minutes to produce a 50.0 ppm solution. The wick member rapidly absorbed water and transported the water into the device causing the metal chlorite and acid to dissolve, traverse the wick divider and react to produce chlorine dioxide in a relatively short amount of time. The chlorine dioxide immediately passed through the membrane shell to form the chlorine dioxide solution.

A number of inventive devices were assembled and tested as described above, except other types of paper towel material were used to form the wick member 24. Each device worked in the desired manner.

EXAMPLE 4

The inventive device was constructed as described above in Example 3. This time, however, each compartment section was filled with 0.25 grams of powdered technical grade sodium chlorite and 0.25 grams powdered citric acid so that the total amount of dry chemicals in the device was 1.0 grams. The pouch was then heat sealed and placed into 500 mL tap water at a temperature of 75° F. The concentration of chlorine dioxide gas was measured with a spectrophotometer by recording the absorbance of the solution at 360 nm and using a molar absorptivity of 1,100 liter per mole-cm. Measurements were taken at five-minute intervals for 10 minutes. The results are shown in Table 4.

TABLE 4

| Time | Concentration |
|---|---|
| 0 min. | 0 ppm |
| 5 min. | 41.48 ppm |
| 10 min. | 79.30 ppm |

Table 4 shows that the device of the present invention produces chlorine dioxide solutions even more quickly than those of the prior art when a mixture of metal chlorite and acid is placed in each compartment section, e.g., it took only 10 minutes to produce a 79.30 ppm solution.

| | PPM $ClO_2$ | | | | |
|---|---|---|---|---|---|
| | Time (Minutes) | | | | |
| | 5 | 10 | 15 | 20 | 25 |
| Example 1 | 2.1 | 5.2 | 8.5 | 11.3 | 16.5 |
| Example 2 | 3.0 | 12.2 | 28.1 | 29.3 | |
| Example 3 | 31.1 | 39.7 | 50.0 | | |
| Example 4 | 41.48 | 79.3 | | | |

Two 2.5"×3" pouches (P1 & P2) were produced in essentially the same manner described in Example 3 above, i.e., each pouch included a membrane shell formed of microporous, hydrophobic non-woven polyethylene sheet material (Tyvek® brand sold by E.I. Du Pont de Nemours & Co.—type 1059B). Pouch P1, however, did not include a wick member.

Each pouch was filled with 0.5 g citric acid and 0.5 g sodium chlorite. In pouch P1, the wick member (made of Scott® brand "Ultrawipes" paper towel) provided a two-compartment pouch and separated the citric acid from the sodium chlorite. In Pouch P2 (no wick divider) the sodium chlorite and citric acid were mixed together in the single compartment provided by the pouch.

Each pouch was tested in a 39-liter test chamber. In each test, the air inside the chamber was exchanged at a rate of 1.3 liters per minute and had a relative humidity of approximately 50%. The chlorine dioxide concentration inside the test chamber was monitored using an Interscan chlorine dioxide meter equipped with an Intech data logger. In each test, the atmosphere inside the test chamber was monitored for chlorine dioxide for ten minutes prior to introduction of the pouch, for two hours while the pouch remained inside the test chamber, and for ten minutes after the pouch was removed. If no chlorine dioxide was detected from the sample, a known chlorine dioxide emitter was placed inside the test chamber to verify the proper function of the test equipment. The results are described below.

Results P1: The chlorine dioxide concentration inside the test chamber never reached detectable limits during the two hour test period. The known chlorine dioxide emitter was placed in the test chamber at the end of the two hour test period and allowed to produce a chlorine dioxide gas concentration of 1.2 ppm chlorine dioxide to confirm test instrument function.

Results P2: Chlorine dioxide gas reached detectable limits within two minutes of sample introduction into the test chamber and reached an equilibrium concentration of about 2.96 ppm $ClO_2$ in about twenty minutes. This suggests a chlorine dioxide production rate of about 0.07 milligrams $ClO_2$ per hour.

The results show that a device constructed according to the present invention with a wick member divider separating the citric acid from the sodium chlorite minimizes or prevents the production of chlorine dioxide gas. Thus, the device of the present invention will not be activated by ambient moisture from the air and will have an extended shelf life.

EXAMPLE 6

The device of the present invention, in a form such as the embodiment shown by FIGS. 1–3, was constructed and compared to the prior art devices shown in Examples 1 and 2. The membrane shell (the panels 22A and 22B) was made of a microporous, hydrophobic non-woven polyethylene sheet material (Tyvek® brand sold by E.I. Du Pont de Nemours & Co.—type 1059B). The wick member 24 was made of Scott® brand "Ultrawipes" paper towel.

The device was approximately 1" by 2" in size and filled with a mixture of 0.5 grams technical grade sodium chlorite of 80% purity and 0.5 grams food grade citric acid. The device was then placed into 500 mL tap water with a temperature of about 73° F. The absorbance of the solution was measured with a spectrophotometer at a wavelength of 360 nm and then converted to a mg/l concentration of chlorine dioxide.

TABLE 5

| Time | Concentration |
| --- | --- |
| 0 min. | 0 mg/l |
| 5 min. | 19.5 mg/l |
| 10 min. | 61.0 mg/l |
| 15 min. | 79.3 mg/l |

As shown by Table 5, this embodiment of the invention performed extremely well.

EXAMPLE 7

The device shown by FIGS. 20–23 was produced as described above. The first chemical unit 112 and second chemical unit 130 were stuck together by peeling the paper off the adhesive strip 140 on the first unit and pressing the units together. The compartment section 118 of the first chemical unit 120 contained approximately 50 grams of technical grade sodium chloride. The compartment section 136 of the second chemical unit 130 contained approximately 25 grams of technical grade, anhydrous citric acid. Double-sided adhesive tape was used to form the adhesive strip 140. The device 20 was then placed in a five-gallon container of tap water. It was observed that chlorine dioxide was generated over time and in an amount similar to the device described in Example 3 above.

The preceding examples can be repeated with similar success by substituting the generically or specifically described components and operating conditions of this invention for those used in the examples.

Although certain preferred embodiments of the invention have been described for illustrative purposes, it will be appreciated that various modifications and innovations of the inventive device may be effected without departure from the basic principals which underlie the invention. Changes of this type are therefore deemed to lie within the spirit and scope of the invention except as may be necessarily limited by the inventive claims and reasonable equivalents thereof

What is claimed is:

1. A device for producing an aqueous chlorine dioxide solution when exposed to water comprising:

a membrane shell defining a compartment which includes one or more dry chemical components capable of producing chlorine dioxide gas when exposed to water; and wick means connected to said membrane shell and extending into said compartment for absorbing water and transporting water into said compartment whereby when said device is exposed to water said wick means absorbs water and transports water into said compartment, said chemical component(s) dissolve in the water and produce chlorine dioxide gas in said compartment, and chlorine dioxide gas exits said compartment through said membrane shell.

2. The device of claim 1 wherein said membrane shell is substantially impervious to liquid and permeable to gas.

3. The device of claim 1 wherein said membrane shell is permeable to liquid and gas.

4. The device of claim 1 wherein said membrane shell is formed of a material selected from the group consisting of polyethylene and polypropylene sheet materials.

5. The device of claim 4 wherein said membrane shell is formed of a microporous, non-woven polyethylene sheet material.

6. The device of claim 1 wherein said wick means is a wick member formed of a material selected from the group consisting cotton pulp and wood pulp.

7. The device of claim 6 wherein said wick member is formed of a non-synthetic fibrous cotton material.

8. The device of claim 1 wherein said compartment includes a metal chlorite component and an acid component whereby when water is transported into said compartment metal chlorite and acid in said compartment dissolve in the water and react to produce chlorine dioxide in said compartment.

9. The device of claim 8 wherein said metal chlorite component comprises a metal chlorite selected from the group consisting of alkali metal chlorites and alkaline earth metal chlorites.

10. The device of claim 9 wherein said metal chlorite component comprises a metal chlorite selected from a group consisting of sodium chlorite, potassium chlorite, barium chlorite, calcium chlorite and magnesium chlorite.

11. The device of claim 10 wherein said metal chlorite component is sodium chlorite.

12. The device of claim 8 wherein said acid component comprises an acid selected from the group consisting of citric acid, lactic acid, tartaric acid, maleic acid, malic acid, glutaric acid, adipic acid, acidic acid, sulfamic acid, formic acid, sulfuric acid, hydrochloric acid and phosphoric acid.

13. The device of claim 12 wherein said acid component is citric acid.

14. The device of claim 8 wherein said acid component comprises an acid precursor that produces an acid when exposed to water.

15. The device of claim 1 wherein said wick means is a wick member having a first end which extends into said compartment and an opposing second end which extends beyond the outer edge of said membrane shell.

16. The device of claim 1 wherein said membrane shell comprises two panel members fastened together to form said compartment.

17. The device of claim 16 wherein said wick means is a wick member which is positioned between and fastened to at least one of said panel members and divides said compartment into first and second compartment sections.

18. The device of claim 17 wherein at least 15% of the outer periphery of said wick member extends beyond the outer periphery of said membrane shell.

19. The device of claim 17 wherein the entire outer periphery of said wick member extends beyond the outer periphery of said membrane shell.

20. The device of claim 17 wherein said compartment includes a metal chlorite component and an acid component, said metal chlorite component being contained within said first compartment section and said acid component being contained within said second compartment section.

21. The device of claim 1 wherein said wick means is a wick member which divides said compartment into first and second compartment sections.

22. The device of claim 21 wherein said compartment includes a metal chlorite component and an acid component, said metal chlorite component being contained within said first compartment section and said acid component being contained within said second compartment section.

23. The device of claim 21 wherein said compartment includes a mixture of a metal chlorite component and an acid component, a portion of said mixture being contained within said first compartment section and a portion of said mixture being contained within said second compartment section.

24. The device of claim 22 further comprising a manually openable ampule, said ampule being positioned in said second compartment section and containing said acid component, said ampule being impervious to water and preventing said acid component from coming into contact with said metal chlorite component until said ampule is manually opened.

25. The device of claim 22 further comprising a manually openable ampule, said ampule being positioned in said first compartment section and containing said metal chlorite component, said ampule being impervious to water and preventing said metal chlorite component from coming into contact said acid component until said ampule is manually opened.

26. The device of claim 21 wherein:
said first compartment section includes a metal chlorite component, said metal chlorite component being sealed in said first compartment section; and
said second compartment section includes an sealable opening therein for allowing an acid component to be placed in said second compartment section prior to exposure of said device to water.

27. The device of claim 21 wherein:
said first compartment section includes an acid component, said acid component being sealed in said first compartment section; and
said second compartment sections includes a sealable opening therein for allowing a metal chlorite component to be placed in said second compartment section prior to exposure of said device to water.

28. The device of claim 1 wherein said compartment includes a metal chlorite component and an acid component, and said device further comprises a manually openable ampule, said ampule being positioned in said compartment and containing said acid component, said ampule being impervious to water and preventing said acid component from coming into contact said metal chlorite component until said ampule is manually opened.

29. The device of claim 1 wherein said compartment includes a metal chlorite component and an acid component, and said device further comprises a manually openable ampule, said ampule being positioned in said compartment and containing said metal chlorite component, said ampule being impervious to water and preventing said metal chlorite component from coming into contact said acid component until said ampule is manually opened.

30. The device of claim 1 wherein said compartment includes a metal chlorite component and has a sealable opening therein for allowing an acid component to be placed in said compartment prior to exposure of said device to water.

31. The device of claim 1 wherein said compartment includes an acid component and has a sealable opening therein for allowing a metal chlorite component to be placed in said compartment prior to exposure of said device to water.

32. The device of claim 1 wherein said wick means is a wick member which divides said compartment into a plurality of compartment sections.

33. The device of claim 1 wherein said wick means comprises at least two wick members, said wick members dividing said compartment into at least two compartment sections.

34. The device of claim 1 further comprising weight means attached to one of said membrane shell and said wick means for causing said device to sink when placed in a body of water.

35. The device of claim 1 further comprising a water-resistant package surrounding and enclosing said membrane shell and said wick means.

36. The device of claim 1 wherein said membrane includes a plurality of openings therein for facilitating the passage of liquid into and out of said device.

37. A device for producing an aqueous chlorine dioxide solution when placed in water comprising:
a membrane shell defining a compartment, said membrane shell allowing the passage of chlorine dioxide gas from said compartment but being impervious to water, said compartment including a metal chlorite component and an acid component;
a wick member connected to said membrane shell, said wick member extending into said compartment and dividing said compartment into a first compartment section containing said metal chlorite component and a second compartment section containing said acid component, said wick member being capable of absorbing water and transporting water into said first and second compartment sections whereby when said device is placed in water said wick member absorbs water and transports water into said compartment, said metal chlorite and acid dissolve in the water, traverse said wick divider, and react to produce chlorine dioxide gas in said compartment, and chlorine dioxide gas passes through said membrane shell.

38. The device of claim 37 wherein said membrane shell is formed of a material selected from the group consisting of polyolefin sheet materials.

39. The device of claim 37 wherein said wick member is formed of non-synthetic fibers of cotton.

40. The device of claim 37 wherein said wick member includes a first end which extends into said compartment and an opposing second end which extends beyond the outer edge of said membrane shell.

41. The device of claim 37 wherein said wick member extends through said compartment and includes a first end extending beyond the outer edge of one side of said membrane shell and a second end extending beyond the outer edge of a second side of said membrane shell.

42. The device of claim 37 wherein the entire outer periphery of said wick member extends beyond the outer periphery of said membrane shell.

43. The device of claim 28 wherein said membrane shell comprises two panel members fastened together to form said compartment.

44. The device of claim 43 wherein said wick member is sandwiched between said panel members.

45. The device of claim 37 further comprising a manually openable ampule, said ampule being positioned in said second compartment section and containing said acid component, said ampule being impervious to water and preventing said acid component from coming into contact with said metal chlorite component until said ampule is manually opened.

46. The device of claim 37 further comprising a manually openable ampule, said ampule being positioned in said first compartment section and containing said metal chlorite component, said ampule being impervious to water and preventing said metal chlorite component from coming into contact said acid component until said ampule is manually opened.

47. The device of claim 37 wherein:
said first compartment section includes a metal chlorite component, said metal chlorite component being sealed in said first compartment section; and
said second compartment section includes a sealable opening therein for allowing an acid component to be placed in said second compartment section prior to placement of said device in water.

48. The device of claim 37 wherein:
said first compartment section includes an acid component, said acid component being sealed in said first compartment section; and said second compartment sections includes an sealable opening therein for allowing a metal chlorite component to be placed in said second compartment section prior to placement of said device in water.

49. The device of claim 37 further comprising means attached to one of said membrane shell and said wick member for causing said device to sink when placed in a body of water.

50. The device of claim 37 further comprising a water-resistant package surrounding and enclosing said membrane shell and said wick member.

51. The device of claim 37 wherein said membrane shell includes a plurality of openings therein for facilitating the passage of liquid into and out of said device.

52. A kit for allowing a device for producing an aqueous chlorine dioxide solution when the device placed in water to be assembled at the point of use comprising:
  a first chemical unit including:
    a first membrane shell;
    a first wick member connected to said first membrane shell and forming a first compartment section between said first membrane shell and said first wick member, said first compartment section containing a metal chlorite component, said first wick member being capable of absorbing water and transporting water into said first compartment section;
  a second chemical unit including:
    a second membrane shell;
    a second wick member connected to said second membrane shell and forming a second compartment section between said second membrane shell and said second wick member, said second compartment section containing an acid component, said second wick member being capable of absorbing water and transporting water into said second compartment section; and
  means attached to at least one of said first chemical unit and said second chemical unit for attaching said first and second chemical units together to assemble said device, whereby when said device is placed in water said first and second wick members absorb water and transport water into said first and second compartment sections, metal chlorite in said first compartment section and acid in said second compartment section contact the water, dissolve in the water, traverse the wick dividers, and react to produce chlorine dioxide in said compartment sections, and said chlorine dioxide passes from said compartment sections through said first and second membrane shells into the water into which the device is placed.

53. The device of claim 52 wherein said first and second membrane shells are formed of a material that is substantially impervious to liquid but allows the passage of gas.

54. The device of claim 52 wherein said first and second membrane shells are formed of a material that allows the passage of liquid and gas.

55. The device of claim 52 wherein said first and second wick members each include at least one end which extends beyond the outer edge of said corresponding membrane shell.

56. The device of claim 52 wherein the entire outer periphery of each of said first and second wick members extends beyond the outer periphery of said corresponding membrane shell.

57. The device of claim 52 wherein said means for attaching said first and second units together includes adhesive material attached to at least one of said first and second wick members.

* * * * *